US009250247B2

(12) United States Patent
Lee et al.

(10) Patent No.: US 9,250,247 B2
(45) Date of Patent: *Feb. 2, 2016

(54) METHODS OF DETECTING ANTIBODIES SPECIFIC FOR DENATURED HLA ANTIGENS

(71) Applicant: ONE LAMBDA, Canoga Park, CA (US)

(72) Inventors: Jar-How Lee, Los Angeles, CA (US); Rui Pei, West Hill, CA (US); Thao Nong, Alhambra, CA (US)

(73) Assignee: ONE LAMBDA, Canoga Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/102,571

(22) Filed: Dec. 11, 2013

(65) Prior Publication Data
US 2014/0099733 A1 Apr. 10, 2014

Related U.S. Application Data

(60) Division of application No. 13/044,430, filed on Mar. 9, 2011, now Pat. No. 8,628,932, which is a continuation-in-part of application No. 12/163,524, filed on Jun. 27, 2008, now Pat. No. 7,972,804.

(60) Provisional application No. 60/947,872, filed on Jul. 3, 2007, provisional application No. 60/949,806, filed on Jul. 13, 2007.

(51) Int. Cl.
G01N 33/543 (2006.01)
G01N 33/68 (2006.01)
G01N 33/50 (2006.01)
C07K 16/28 (2006.01)

(52) U.S. Cl.
CPC ........ G01N 33/6854 (2013.01); C07K 16/2833 (2013.01); G01N 33/505 (2013.01); G01N 33/543 (2013.01); G01N 2800/245 (2013.01); Y10T 436/25125 (2015.01)

(58) Field of Classification Search
CPC ............ G01N 33/6854; G01N 33/505; G01N 33/543; G01N 2800/245; C07K 16/2833; Y01T 436/25125
USPC .............. 435/7.1, 7.24, 7.92, 287.2; 436/506, 436/507, 517, 518, 523, 524, 528, 172, 175, 436/177, 800, 811; 422/73, 430, 82.05
See application file for complete search history.

(56) References Cited

U.S. PATENT DOCUMENTS

| 4,722,891 | A | 2/1988 | Drutz et al. | |
|---|---|---|---|---|
| 5,420,013 | A | 5/1995 | Pouletty et al. | |
| 5,948,627 | A | 9/1999 | Lee et al. | |
| 6,150,122 | A | 11/2000 | Lee et al. | |
| 6,514,714 | B1 | 2/2003 | Lee et al. | |
| 7,972,804 | B2 * | 7/2011 | Lee et al. | 435/7.24 |
| 8,628,932 | B2 * | 1/2014 | Lee et al. | 435/7.24 |

| 2004/0126829 | A1 | 7/2004 | Hildebrand et al. |
|---|---|---|---|
| 2004/0137537 | A1 | 7/2004 | Montero-Julian et al. |
| 2005/0059095 | A1 | 3/2005 | Yang et al. |
| 2007/0037195 | A1 | 2/2007 | Ho |
| 2009/0011437 | A1 | 1/2009 | Lee et al. |

OTHER PUBLICATIONS

Pei et al. Detection of Antibodies against B2-microglobulin free HLA Heavy Chains Using Flow PRA Beads, Visuals Clinical Histocompatibility Workshop: 9-10 (2000).*
Bangs Laboratory Inc. "Product Data Sheet 706—COMPLEM®", dated Aug. 10, 2009.
International Preliminary Report on Patentability issued in connection with International Application No. PCT/US2012/028272, dated Mar. 28, 2014.
Bayer et al., Protein biotinylation. Meth. Enzymol. 184: 138-63 (1990).
Bix et al., Functionally conformed free class I heavy chains exist on teh surface of beta 2 microglobulin negative cells. J. Exp. Med. 176: 829-34 (1992).
Choo, The HLA system: Genetics, immunology, clinical testing, and clinical implications. Yonsei Med. J. 48: 11-23 (2007).
Kahn et al., Anti-HLA antibodies detected by CDC associated with lower survival after lung transplant. Medscape Medical News (2006).
Krangel et al., Assembly and maturation of HLA-A and HLA-B antigens in vivo. Cell, 18: 979 (1979).
Noreen, Interpretation of crossmatch tests. The American Society for Histocompatibility and Immunogenetics Laboratory Manual, 3rd Edition, I.C.1.1-1.C.1.13 (1994).
Pei et al., Detection of antibodies against B2-microglobulin free HLA heavy chains using flow PRA beads. Visuals Clinical Histocompatability Workshop, 9-10 (2000).
Perosa et al., Beta 2-microglobulin-free HLA class I heavy chain epitope mimicry by monoclonal antibody HC-10-specific peptide. J. Immunol. 171: 1918-26 (2003).
Schnabl et al., Activated human T lymphocytes express MHC class I heavy chains not associated with beta 2-microglobulin. J. Exp. Med. 171: 1431-42 (1990).
Sugawara et al., A simple method to eliminate the antigenicity of surface class I MHC molecules from the membrane of viable cells by acid treatment at pH 3. J. Immunol. Meth. 100: 83-90 (1987).
Tampé et al., Reactions of the subunits of the class II major histocompatibility complex molecule IAd. Proc. Natl. Acad. Sci. US A. 88: 10667-70 (1991).
Terasaki et al., Microdroplet assay of human serum cytotoxins. Nature. 204: 998-1000 (1964).
International Search Report and Written Opinion of the International Searching Authority issued in connection with corresponding International Application No. PCT/US2008/068605, dated Sep. 29, 2008.
International Preliminary Report on Patentability issued in connection with International Application No. PCT/US2008/068605, dated Jan. 5, 2010.

* cited by examiner

Primary Examiner — Gail R Gabel
(74) Attorney, Agent, or Firm — Marshall, Gerstein & Borun LLP

(57) ABSTRACT

The invention is directed to methods of screening for HLA antibodies comprising detecting antibodies specific for native HLA antigens and denatured HLA antigens. The invention also provides for methods of removing antibodies specific for denatured HLA antigens or antibodies specific for native HLA antigens from a serum sample. In addition, the invention also provides for method of predicting whether a transplant recipient has an increased risk for rejecting the transplanted organ.

7 Claims, 9 Drawing Sheets

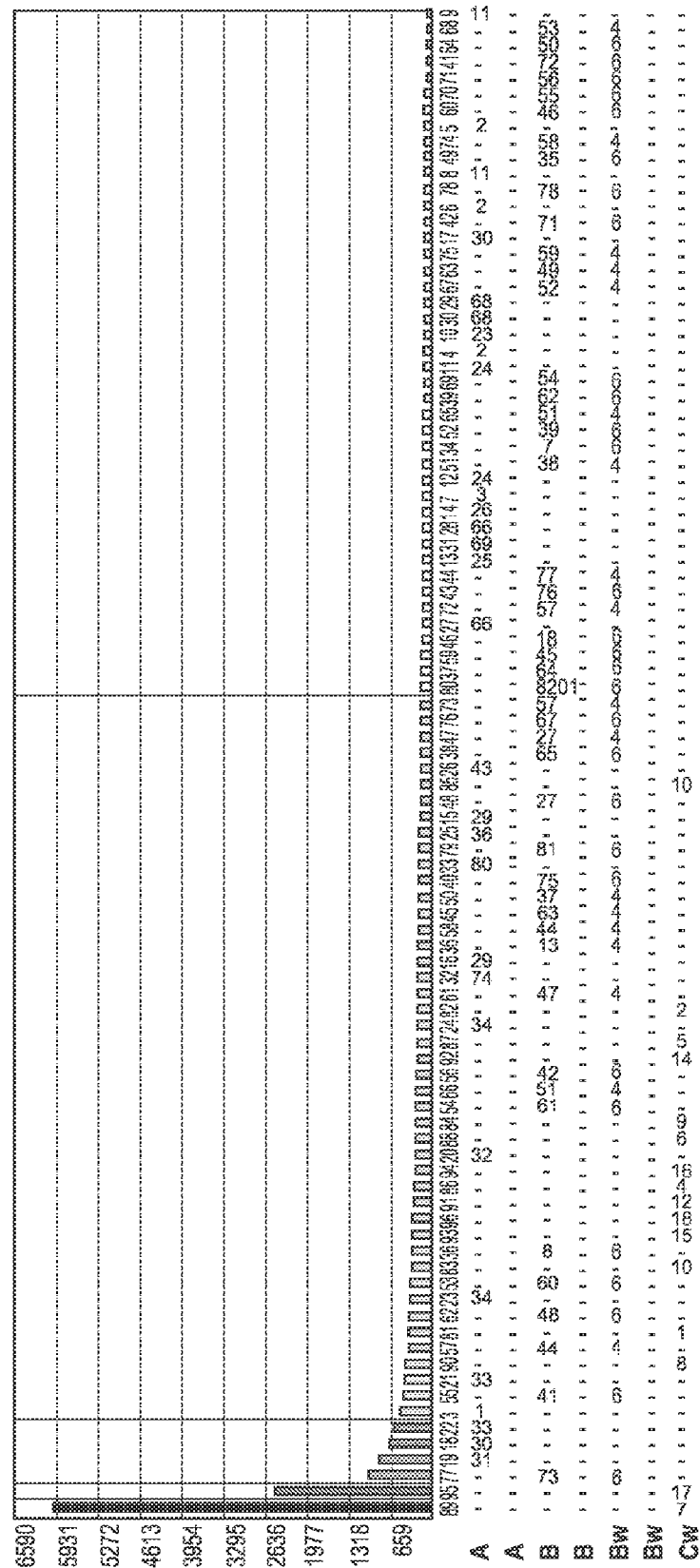

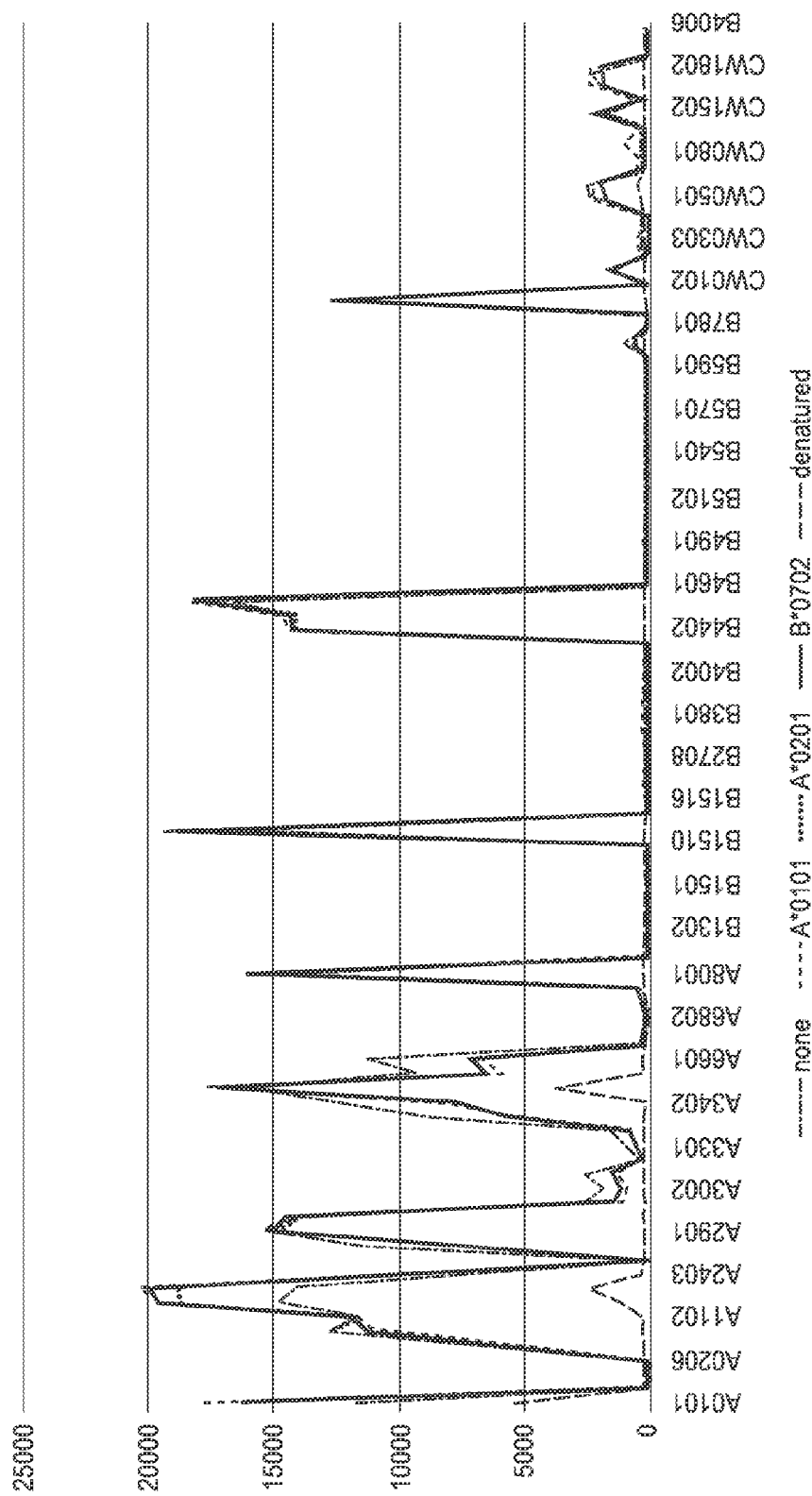

METHODS OF DETECTING ANTIBODIES SPECIFIC FOR DENATURED HLA ANTIGENS

This application is a continuation of U.S. patent application Ser. No. 13/011,430, filed (now U.S. Pat. No. 8,628,932) which is a continuation-in-part application of U.S. patent application Ser. No. 12/163,524, filed Jun. 27, 2008 (now U.S. Pat. No. 7,972,804), which claims priority benefit of U.S. Provisional Patent Application No. 60/947,872, filed Jul. 3, 2007 and U.S. Provisional Patent Application No. 60/949, 806, filed Jul. 13, 2007, all of which are incorporated by reference herein in their entirety.

FIELD OF INVENTION

The invention is directed to methods of screening for HLA antibodies comprising detecting antibodies specific for native HLA antigens and denatured HLA antigens. Native class I HLA antigens are non-covalently associated with β2-microglobulin and denatured HLA class I antigens are disassociated from β2-microglobulin. Native HLA class II antigens are non-covalently bound hetero-dimers and denatured HLA class II antigens are monomers. The invention also provides for methods of removing antibodies specific for denatured HLA antigens or antibodies specific for native HLA antigens from a serum sample. In addition, the invention provides for methods of predicting whether a transplant recipient has an increased risk for rejection of the transplanted organ or has an increased risk for developing graft vs. host disease.

BACKGROUND

Transplant rejection occurs when the immune system of the recipient of a transplant, particularly antibodies produced by the recipient, attacks the transplanted organ or tissue. The recipient's immune system recognizes the transplanted organ as foreign tissue and attempts to destroy it. Rejection also occurs when the transplanted organ comprises the donor's lymphocytes or progenitor stem cells, which may generate an immune response to the recipient tissues such as graft vs. host disease. Chronic rejection is a term used to describe all long term loss of function in organ transplants associated with chronic alloreactive immune response. Long term chronic rejection usually leads to a need for a new transplanted organ about a decade after the initial transplant. Human leukocyte antigens (HLA) are one type of molecules within a transplanted organ in which the recipient's immune system attacks that causes a transplant rejection.

An HLA class I molecule consists of a 45-kDa glycoprotein (heavy chain) non-covalently associated with a 12-kDa polypeptide, β2-microglobulin (β2m). Association of β2m with newly synthesized class I heavy chains is required in order for the HLA molecule to transport and present the peptide (Krangel et al., Cell 18: 979, 1979). However, β2m free class I heavy chains were identified on activated T lymphocytes (Schnabl et al., J. Exp. Med. 171:1431, 1990) and other cell surfaces (Bix & Raulet, J. Exp. Med. 176(3) 829-34, 1992). Properly conformed β2m free class I heavy chains were identified on the cells and were believed to have functional importance. β2m can be dissociated from a HLA class I complex on a cell surface by acid treatment (Sugawara et al., J. Immunol. Methods, 100(1-2):83-90, 1987). β2m can also be dissociated from HLA Class I complex coated on microbeads using the similar method of low pH treatment. (Pei et al. Visuals Clinical Histocompatability Workshop 2000, 9-10). Those β2m-free HLA heavy chains are referred to as "denatured antigens." Antibodies against denatured class I HLA antigens have been detected in human sera from non-sensitized donors, however, they have not been well studied and currently the clinical significance of these antibodies is unclear.

HLA class II molecules are heterodimers formed by non-covalent linkage of two glycosylated polypeptide chains referred to as alpha and beta chains. The α subunit is 33 kDa and the β subunit is 28 kDa, and both chains are transmembrane polypeptides that have the same overall structure. The invariable α chain is encoded by the DRA HLA gene and this chain binds various β chains encoded by the DRB HLA genes. In addition, the DP and Dq HLA gene families each have one gene that encodes an α chain and a β chain. (Reviewed in Choo, Yonsei Med. J. 48: 11-23, 2007).

Cell-based assays are the most widely accepted assay for cross-matching HLA antigens, and these assays are used to determine if a recipient has antibodies in their serum that are cytotoxic to the lymphocytes of a prospective donor. The donor cells for the cross-match assay are collected from either blood or spleen and must be alive, while the recipient serum can be frozen prior to the assay. Exemplary standard procedures for cross-matching include complement-dependent cytotoxicity test (CDC), CDC with antiglobulin augmentation (AHG) and flow Cytometry Cross-match (FC) (Noreen, The American Society for Histocompatibility and Immunogenetics Laboratory Manual, 3rd Ed, I.C.1.1-I.C.I.13).

As the number of identified HLA antigens is continuously increasing, a cell panel must be extremely large to screen for all known HLA antigens in a single assay. In addition, the cell-based assays may be neglecting clinically important antigens as about 50% of transplanted organs will be chronically rejected over a long period of time (known as "long tem chronic organ rejection"). Cell-based assays are also limited by the fact that the target cells isolated under the normal condition bear only HLA antigens in their native conformation such as β2m-associated class I antigens (Sugawara et al., J. Immunol. Methods, 100(1-2):83-90, 1987) and heterodimeric class II antigens. Thus, the cell-based assays will not detect antibodies specific for denatured HLA antigens.

The development of solid-phase HLA antibody detection assays, such as bead-based assays, allow for screening of many HLA antigens in one assay. Therefore, many laboratories are using solid-phase HLA antibody detection assays and virtual cross-matching assays in addition to cell-based assays. "Virtual cross-matching" is a procedure that predicts the result of a cell-based cross-match assay. Virtual cross-matching is carried out by comparing the donor antigen profile (donor tissue typing) and the recipient HLA antibody profile as determined by solid-phase assays described herein. For example, some laboratories first screen the recipient sera using a solid-phase assay to determine potential donors matches and subsequently use a cell-based assay for the cross match analysis of the donor cells and recipient sera. With the current screening procedures, sera that is positive for antibodies specific for donor HLA antigens in both the solid-phase assay and the cell-based assay is certain not to be an appropriate match for transplant. However, if the recipient sera is positive for antibodies specific for the donor HLA antibodies in the solid-phase assay but negative in the cell-based assay, there is uncertainty whether this sera is false-positive for HLA-antibodies and whether the tissue can be used for transplant.

One of the advantages of determining the HLA antibody profile using solid-phase assays is that this information can be stored for the transplant recipients. Therefore, biological samples do not need to be acquired at the same time or need to be in the same location for analysis. The HLA antibody profiles will allow for analysis before an organ is shipped for transplant. In addition, solid-phase HLA antigen analysis can screen many more donors and recipient pairs and may screen many more antigens at one time or in fewer assays. In addition, these assays may decrease the incidence in which a positive cross-match organ is shipped for transplant before the determination.

As increasing numbers of sera samples were tested for HLA antibodies, there was a significant increase in the number of samples that were positive using the solid-phase assay but negative using cell-based cross-match assays. In addition, antibodies to denatured class I HLA antigens are known to be present in the human sera and particularly some untransfused males have been shown to have HLA antibodies in their sera.

It is known that acid treated cells, which dissociated $\beta m2$ from the surface of HLA class I molecule, can be used to detect antibodies specific for denatured HLA antigens. In addition, panels of microbeads that present denatured class I HLA antigens have been generated and used to detect antibodies specific for these denatured antigens (See Pei et al. Visuals Clinical Histocompatability Workshop 2000, 9-10).

Currently, those of skill in the art do not consider antibodies specific for denatured HLA antigens to induce transplant or transfusion rejections. Generally, the presence of denatured HLA antigens is considered an artifact of sample preparation and detection of antibodies specific for these denatured antigens is not considered a clinically significant step of HLA tissue-typing analysis. One reason for this view is that cell-based assays are the current standard assay for cross-matching, and there are no current assays available for detecting antibodies specific for denatured antigens alone. As virtual cross-matching and solid-phase assays become standard practices in tissue-typing laboratories, there is a need to develop assays that screen for antibodies specific for HLA antigens while determining whether the antibodies are specific for native or denatured antigens. In addition, there is a need to decrease the number of false positive and false negative results of both solid-phase and cell-based tissue typing assays.

SUMMARY OF INVENTION

The invention provides for methods of screening for HLA antibodies which comprise preparing a panel of solid-phase substrates, wherein each substrate presents at least one selected native HLA antigen or at least one selected denatured HLA antigen. Even though the art provides for methods of detecting antibodies specific for denatured HLA antigens and it is likely that panels of HLA antigens currently used in the art present some denatured antigens mixed with native antigens, the need to distinguish between antibodies specific for denatured HLA antigens and native HLA antigens was not recognized. The present invention is the first to provide methods of screening for antibodies specific for HLA antigens using solid-phase substrates that present a selected native HLA antigen or a selected denatured HLA antigen, and is the first method wherein the denatured HLA antigens are separated from native HLA antigens and concentrated on a substrate. The clinical significance of antibodies specific for denatured HLA antigens was unknown and therefore the available screening methods did not focus on selectively detecting these antibodies.

It is important to screen for antibodies that specifically bind to denatured antigens, because there is a chance that a transplant recipient may have a high reactivity to a denatured HLA antigen and may not have the same reactivity for the antigen in its native conformation. Cell-based screening assays are unlikely to detect the presence of antibodies that specifically bind to denatured HLA antigens because there is minimal presentation of denatured antigens on the cell surface. Failure to detect a high reactivity to a denatured HLA antigen increases the risk for rejection of the transplanted organ. Therefore, screening for denatured antigens is an important step in fully analyzing a transplant recipient for HLA antigen reactivity prior to transplant.

In addition, many laboratories are carrying out virtual cross-matching assays and solid-phase assays in conjunction with standard cell-based assays. For virtual cross-matching to be effective, the HLA antibody and antigen profiles of the transplant or transfusion recipients and donors should include information regarding denatured HLA antigens and antibodies thereto. Antibodies to denatured HLA antigens have been detected in untransfused transplant recipients. These findings suggest that the cell-based assays may be missing clinically significant antibodies to denatured HLA antigens and these antibodies may play a role in previously unexplained transplant rejections. On the other hand, detection of serum reactivity due to antibodies that specifically bind denatured HLA antigens rather than native antigens in a virtual cross-matching assay may be a false positive result that would not be detected in a cell-based assay. These false positive results may negatively affect transplant organ allocation by labeling a transplant patient ineligible due to an inaccurate HLA antibody profile.

The methods of the invention may be carried out with any type of HLA antigen including class I and class II HLA antigens. The term "native HLA antigen" refers to a HLA antigen that is in a conformation that is a stable three-dimensional structure that determines the protein's biological function. A native HLA class I molecule consists of a 45 kDa glycoprotein which is non-covalently associated with $\beta 2$-microglobulin ($\beta 2m$). A native HLA class II molecule consists of the antigen in a heterodimeric conformation. The term "denatured HLA antigen" refers to a HLA molecule that is not in its native conformation. A denatured HLA class I antigen is disassociated from $\beta 2m$ and a denatured HLA class II antigen is in a monomeric conformation.

In one embodiment, the invention provides for methods of screening for antibodies that specifically bind native HLA antigens or denatured HLA antigens, comprising the steps of: a) preparing a panel of solid-phase substrates, wherein the panel comprises substrates that present at least one selected native HLA antigen and substrates that present at least one selected denatured HLA antigen, b) obtaining a serum sample from a human subject, c) contacting each panel with the serum sample and f) detecting binding of an antibody to the panel, wherein binding of an antibody to a solid-phase substrate presenting a denatured HLA antigen is indicative of a human subject having antibodies specific for a selected denatured HLA antigen, and wherein binding of an antibody to a solid-phase substrate presenting a selected native HLA antigen is indicative of a human subject having antibodies specific for a selected HLA antigen.

The term "selected HLA antigen" refers to intentionally presenting a particular HLA antigen on the solid-phase substrate. Unlike current methods in the art, the invention provides for intentionally presenting particular denatured HLA antigens or particular native HLA antigens on solid-phase substrates in order to distinguish whether a donor has antibodies that specifically bind to denatured HLA antigens, native HLA antigens or both.

The term "selected denatured HLA antigens" refers to intentionally presenting a particular HLA antigen on a solid-phase substrate and intending to denature the antigen either while associated with the solid-phase substrate or prior to being associated to the solid-phase substrate. In preferred embodiments, the treatment to denature the HLA antigen will cause all or predominantly all of the HLA antigens presented on the solid-phase substrate to be in a denatured conformation. Therefore, binding of an antibody to the solid-phase substrate presenting a selected denatured antigen is indicative of a human subject having antibodies specific for a selected denatured HLA antigen.

The term "selected native HLA antigens" refers to intentionally presenting a particular native HLA antigen on a solid-phase substrate. It is preferred that the selected native HLA antigens are predominantly in their native conformation, however, some embodiments may contain a mixture of native and denatured antigens. Therefore, an antibody that binds to a solid-phase substrate presenting a selected native antigen is indicative of a human subject having antibodies specific for a selected HLA antigen, which may be in native conformation or in denatured conformation. Techniques to separate the native and denatured HLA antigens while coated on a solid-phase substrate are one method of preparing a solid-phase panel presenting predominantly native HLA antigens.

The invention also provides for methods of screening for antibodies that specifically bind HLA antigens in the native conformation, antibodies that specifically bind HLA antigens that are denatured and antibodies that specifically bind a HLA antigen in both its native and denatured conformation. These methods involve contacting a serum sample with a solid-phase substrate or cell that present the HLA antigen to absorb the antibodies that bind the HLA antigen in the opposing conformation prior to screening (contacting and detecting binding) for the HLA specific antibodies of interest. For example, when screening for antibodies that specifically bind a HLA antigen in its native conformation, the sera will first be contacted to a cell or solid-phase substrate presenting the HLA antigen that has been denatured in order to remove antibodies that specifically bind the denatured HLA antigen to generate a serum sample essentially free of antibodies that specifically bind the denatured HLA antigen. Alternatively, when screening for antibodies that bind a HLA antigen in its denatured conformation, the sera will first be contacted to a cell or solid-phase substrate that presents the HLA antigen in its native conformation in order to remove antibodies that specifically bind the native HLA antigen to generate a serum sample that is essentially free of antibodies that specifically bind to said native HLA antigens.

In one embodiment, the invention provides for methods of screening for antibodies that specifically bind a native HLA antigen, comprising the steps of: a) obtaining a serum sample from a human subject, b) providing a first solid-phase substrate having immobilized thereon said HLA antigen which has been denatured, c) binding antibodies that specifically bind said denatured HLA antigen in said serum sample to said first solid-phase substrate to form an antibody/antigen complex, d) separating the antibody/antigen complex from the serum sample to generate a serum sample essentially free of antibodies that specifically bind said denatured HLA antigen, e) contacting the serum sample that is essentially free of antibodies that specifically bind said denatured HLA antigen with a second solid-phase substrate presenting the native HLA antigen, and f) detecting binding of an antibody to the second solid-phase substrate, wherein binding of an antibody is indicative of a human subject having antibodies that specifically bind the native HLA antigen.

In another embodiment, the invention provides for methods of screening for antibodies that specifically bind a native HLA antigen, comprising the steps of: a) obtaining a serum sample from a human subject, b) providing a cell that presents said HLA antigen which has been denatured, c) binding antibodies that specifically bind said denatured HLA antigen in said serum sample to said cell to form an antibody/antigen complex, d) separating the antibody/antigen complex from the serum sample to generate a serum sample essentially free of antibodies that specifically bind said denatured HLA antigen, e) contacting the serum sample that is essentially free of antibodies that specifically bind said denatured HLA antigen with a solid-phase substrate presenting the native HLA antigen, and f) detecting binding of an antibody to the solid-phase substrate presenting the native HLA antigen, wherein binding of an antibody is indicative of a human subject having antibodies that specifically bind the native HLA antigen.

The invention also provides for methods of screening for antibodies that specifically bind a HLA antigen that has been denatured, comprising the steps of: a) obtaining a serum sample from a human subject, b) providing a first solid-phase substrate having immobilized thereon said HLA antigen in its native conformation, c) binding antibodies that specifically bind said native HLA antigen in said serum sample to said first solid-phase substrate to form an antibody/antigen complex, d) separating the antibody/antigen complex from the serum sample to generate a serum sample essentially free of antibodies that specifically bind said native HLA antigen, e) contacting the serum sample that is essentially free of antibodies that specifically bind said native HLA antigen with a second solid-phase substrate presenting the HLA antigen that has been denatured, and f) detecting binding of an antibody to the second solid-phase substrate, wherein binding of an antibody is indicative of a human subject having antibodies that specifically bind the denatured HLA antigen.

In another embodiment, the invention provides for methods of screening for antibodies that specifically bind a HLA antigen that has been denatured, comprising the steps of: a) obtaining a serum sample from a human subject, b) providing a cell that presents said HLA antigen in its native conformation, c) binding antibodies that specifically bind said native HLA antigen in said serum sample to said cell to form an antibody/antigen complex, d) separating the antibody/antigen complex from the serum sample to generate a serum sample essentially free of antibodies that specifically bind said native HLA antigen, e) contacting the serum sample that is essentially free of antibodies that specifically bind said native HLA antigen with a solid-phase substrate presenting the HLA antigen that has been denatured, and f) detecting binding of an antibody to the solid-phase substrate, wherein binding of an antibody is indicative of a human subject having antibodies that specifically bind the denatured HLA antigen.

The invention further provides for methods of screening for antibodies that specifically bind HLA antigens that comprising various permutations and combination of any of the preceding methods. One of skill in the art will recognize that any number or combination of the steps can be used to characterize a serum sample in regards to anti-HLA antibody profiles. For example, it may be of interest to screen a serum sample for antibodies that bind to a HLA antigen in its native conformation, and then absorb the antibodies that specifically bind to said HLA antigen that is denatured and then detect if the resulting serum (that is essentially free of antibodies that specifically bind the denatured HLA antigen) continues to bind to a solid-phase panel that present the HLA antigen in its native conformation.

Further, serum samples may comprise antibodies that specifically bind a HLA antigen in its native and denatured conformation. In this example, a skilled artisan will understand that the absorption step may strip the serum of transplant relevant antibodies, thus carrying out a combination of the steps of screening methods is necessary to ensure the proper controls are run to ensure the results are true positives or true negatives.

A serum sample may be polyclonal for a particular HLA antigen and therefore comprise one or more of the following: antibodies that bind a HLA antigen in its native conformation, antibodies that bind said HLA antigen in its denatured conformation and antibodies that bind said HLA antigen in its native and denatured conformation. One of skill in the art will appreciate that the steps of the preceding screening methods can be combined in different manners to distinguish between sera that comprises antibodies that bind a HLA antigen in its native conformation, an antibody that binds a HLA antigen in its denatured conformation or an antibody that binds a HLA antigen in both its native and denatured conformation.

The absorption step of any of the preceding methods of screening may be carried out with cells that express the HLA antigen in a native or denatured conformation. The cells may endogenously express the HLA antigen such as platelets or leukocytes. In addition, cells may be engineered to recombinantly express the HLA antigens (in either the native or denatured conformation) on the cell surface. These cells may not endogenously express the HLA antigen or express the HLA antigen at low level. Furthermore, cells that endogenously express the HLA antigen in a native or denatured conformation may be engineered to recombinantly express the HLA antigen at levels greater than endogenous expression.

A solid-phase substrate that presents a HLA antigen in its native conformation may also present a HLA antigen in its denatured conformation as an artifact of sample preparation. However, the number of denatured antigens on the solid-phase substrate in this situation should be much lower than the number of native HLA antigens. Thus, when carrying out the absorption step of any of the preceding screening methods, one of skill in the art will appreciate that any effect of underlying denatured HLA antigens may be effectively removed by titrating the volume of test sera and the immunosorbents.

The methods of screening for antibodies that specifically bind native HLA antigens and antibodies that specifically bind denatured HLA antigens are useful for characterizing the HLA antibody profile determined by solid-phase assays or virtual cross-matching assays. These methods assist in determining whether a result is a true positive, true negative, false positive or false negative. As more laboratories are using solid-phase assays and virtual cross-matching, these methods will be a valuable tool for analyzing the results.

In another embodiment, the invention provides for methods of predicting whether a transplant recipient has an increased risk for rejection of the transplanted organ comprising the steps of: a) determining HLA antibody profile of the recipient using a solid-phase assay comprising a panel of solid-phase substrates wherein the panel comprises substrates that present at least one selected native HLA antigen and substrates that present at least one selected denatured HLA antigen, b) determining HLA antigen profile of the donor of the transplanted organ, c) comparing the recipient HLA antibody profile and the donor HLA antigen profile, wherein a positive result is when the HLA antigen profile indicates the recipient sera contains an antibody specific for a HLA antigen within the donor HLA antigen profile and a negative result is when the HLA antibody profile indicates the recipient sera does not contain an antibody specific for a HLA antigen within the donor HLA antigen profile, d) cross-matching the recipient sera and the donor tissue, wherein a positive result is when the recipient sera contains antibodies specific for a HLA antigen on the donor tissue and a negative result is when the recipient sera does not contain antibodies specific for a HLA antigen on the donor tissue, and e) predicting whether the recipient has an increased risk for rejection of the transplanted organ, wherein an increased risk for rejection of the transplanted organ is predicted when the HLA antibody profile determined by the solid-phase assay is positive and the cross-match is negative. The invention include methods of predicting long term chronic rejection.

The method of predicting whether a transplant recipient has an increased risk for rejection may further comprise a step of selecting a donor by comparing the recipient antibody profile with the donor HLA antigen profile, wherein the donor antigen profile is determined using a solid-phase assay that comprises a panel of solid-substrates presenting antibodies specific for HLA antigens.

In another embodiment, the invention provides for methods of predicting whether a transplant recipient has an increased risk for developing graft vs. host disease comprising the steps of: a) determining HLA antibody profile of the donor of the transplanted organ using a solid-phase assay comprising a panel of solid-phase substrates wherein the panel comprises substrates that present at least one selected HLA antigen and substrates that present at least one selected denatured antigen, b) determining HLA antigen profile of the recipient of the transplanted organ, c) comparing the donor HLA antibody profile and the recipient HLA antigen profile, wherein a positive result is when the HLA antibody profile indicates the donor sera contains an antibody specific for a HLA antigen within the recipient HLA antigen profile and a negative result is when the HLA antibody profile indicates the donor sera does not contain an antibody specific for a HLA antigen within the recipient HLA antigen profile, d) cross-matching the donor sera and the recipient tissue, wherein a positive result is when the donor sera contains antibodies specific for a HLA antigen on the recipient tissue and a negative result is when the recipient sera does not contain antibodies specific for a HLA antigen on the donor tissue, and e) predicting whether the recipient has an increased risk for developing graft vs. host disease, wherein an increased risk for graft vs. host disease is predicted when the HLA antibody profile determined by the solid-phase assay is positive and the cross-match is negative. This method is preferably carried out wherein the recipient is in need of a bone marrow transplant, liver transplant or transplant of any organ that contains progenitor stem cells or lymphocytes.

The method of predicting whether a transplant recipient has an increased risk for developing graft vs. host disease may further comprise a step of selecting a recipient by comparing the recipient antigen profile with the donor HLA antibody profile, wherein the recipient antigen profile is determined using a solid-phase assay that comprises a panel of solid-substrates presenting antibodies specific for HLA antigens.

The cross-match assay may be carried out using any cell-based antibody detection assay in known in the art. Exemplary cross-match assays are the complement-dependent cytotoxicity test (CDC), CDC with antiglobulin augmentation (AHG) and flow Cytometry Cross-match (FC) (See Noreen, The American Society for Histocompatibility and Immunogenetics Laboratory Manual, 3rd Ed, I.C.1.1-I.C.I.13).

A "positive" result in a cell-based cross-match assay is when an antibody in the recipient sera binds to a donor cell. In cytotoxic cell-based cross-match assays, a "positive" result is when the recipient sera is cytotoxic to the donor cells, which indicates the sera contained antibodies specific for the HLA antigens on the donor cells. The FC cross-match assay uses donor cells and recipient sera, however a "positive" result is detected by a fluorescently labeled secondary antibody that binds to the complex of the recipient antibody binding to the donor cells. The binding of the secondary antibody causes a channel shift detected by a flow cytometer.

A "negative" result in a cell-based cross-match assay is when the recipient sera does not contain antibodies that bind to the donor cells, which suggest that the recipient will not reject the donor's tissue upon transplantation. In a cytotoxic cell-based cross-match assay, a negative result is when the recipient sera is not toxic to the donor cells. In the FC cross-match assay, a negative result is when a donor cell/recipient antibody complex is not generated and therefore the secondary antibody does not bind the complex and a channel shift does not occur.

The solid-phase assay or a virtual cross-match assay allows the recipient sera to be tested for antibodies that will bind to HLA antigens presented on a solid substrate and thereby determine the "HLA antibody profile" for the transplant recipient. The donor tissue is typed using serology methods or DNA-based methods to determine the donor's "HLA antigen profile." The serology assays use known antibodies to detect the HLA antigens within a donor tissue, such as the microlymphocytotoxicity assay, as described in Terasaki et al. *Nature* 204: 998-1000, 1964, which uses serum having known HLA specificity and donor lymphocytes. DNA-based assays will use PCR or hybridization methods to determine the HLA antigens within a donor tissue. These assays are considered "virtual" because the recipient sera and donor tissue are not contacted and tested directly. A "positive" result of the virtual cross-match assay or a solid-phase assay is when the recipient HLA antibody profile indicates the presence of a HLA antibody within the sera that is specific for a HLA antigen within the donor's HLA antigen profile. A "negative" result of the virtual cross-match assay or a solid-phase assay is when the recipient HLA antibody profile indicates that the recipient does not have antibodies specific for the HLA antigens within the donor's HLA antigen profile.

The methods of the invention may be carried out with any solid-phase substrate. In preferred embodiments, the methods are carried out with solid-phase panels comprising a set of microparticles or microbeads, wherein each microparticle presents at least one HLA antigen.

The detection steps of the methods of the invention may be carried out with any technique that recognizes antibody binding to a solid-phase substrate. In preferred embodiments, the detection steps are carried out using a flow cytometer and/or a secondary antibody. Exemplary secondary antibodies include those which comprise a label selected from the group consisting of a radioactive label, fluorescent label, enzymatic label, avidin label or biotin label.

The methods of the invention are carried out with a serum sample obtained from a human subject. In preferred embodiments, the serum sample is obtained from a transplant or transfusion recipient or a transplant or transfusion donor.

In a further embodiment, the invention provides for kits to carry out the methods of the invention. The invention provides for kits used to screen for antibodies that specifically bind to a denatured HLA antigen and/or a native HLA antigen, comprising a panel of solid-phase substrates, wherein the panel comprises substrates that present at least one selected native HLA antigen and substrates that present at least one selected denatured HLA antigen. In addition, the invention provides for kits used to predict whether a transplant recipient has an increased risk of rejecting the transplanted organ comprising a panel of solid-phase substrates, wherein the panel comprises substrates that present at least one selected native HLA antigen and substrates that present at least one selected HLA denatured antigen. Then invention also provides for a kit for predicting whether a transplant recipient has an increased risk of developing graft vs. host disease, comprising a panel of solid-phase substrates wherein the panel comprises substrates that present at least one selected native HLA antigen and substrates that present at least one selected denatured HLA antigen.

When preparing a panel of HLA antigens for screening biological samples, the techniques used to associate HLA antigens to a solid substrate results in the association of a mixture of native HLA antigens and denatured HLA antigens. In the past, the clinical significance of the presence of denatured HLA antigens and antibodies specific for these denatured HLA antigens was not recognized, and therefore, the generation of a mixture of native and denatured HLA antigens was not considered important. The teachings herein demonstrate the need to distinguish between native and denatured HLA antigens. Therefore, the invention provides for methods of removing denatured HLA antigens or native HLA antigens from a sample.

The method of removing denatured HLA antigens from a sample comprise the steps of: contacting a sample with an antibody specific for denatured HLA antigens to form a complex comprising the denatured HLA antigen and the antibody, and separating the complex from the sample, wherein the separation removes the denatured HLA antigens from the sample. This method may further comprise the step of isolating the native HLA antigen from the sample and optionally presenting the native HLA antigen on a solid-phase substrate. The method of removing native HLA antigens from a sample, comprises the steps of: contacting the sample with an antibody specific for native HLA antigens to form a complex comprising the native HLA antigen and the antibody, and separating the complex from the sample, wherein the separation removes the native HLA antigens from the sample.

This method of removing denatured HLA antigens or native HLA antigens may further comprise the step of isolating from the sample the denatured or native HLA antigens that remain in the sample after the separation, and optionally presenting these isolated denatured or native HLA antigens on a solid-phase substrate. In one embodiment, the contacting step of these methods is carried out with an antibody that is bound to an affinity column.

In another embodiment, the invention provides for methods of removing denatured antigens from a sample comprising contacting the sample with a blocking agent, such as a blocking antibody, wherein binding of the denatured antigen to the blocking agent removes the antigen from the sample. The blocking effectively results in an antigen that cannot bind to antibodies specific for the antigen within a biological sample, and therefore only native HLA antigens are available for detection in the screening assay.

The denatured HLA antigens or native HLA antigens may be removed from any sample that comprises HLA antigens derived from such as a cell sample including mammalian, insect or bacteria cells expressing recombinant HLA antigens, tissue sample, blood sample or serum sample. Exemplary samples that contain HLA antigens include cell lysates, tissue lysates, tissue homogenates and cell culture media into which recombinant HLA antigen are expressed. The samples of the invention include purified HLA antigens from various sources such as recombinant antigens expressed by bacteria, insect cells or mammalian cells, for example transformed bacteria may express HLA antigen within inclusion bodies, and the cell lysates or cell culture media containing these inclusion bodies may be used as a sample for these methods.

The antigens in the samples may be denatured due to sample preparation or may be intentionally denatured prior to the contacting step of the methods. The antigens may be denatured using an acidic denaturing buffer such as a buffer containing 0.3M Glycine-HCl pH 2.7 with 1% BSA.

The invention also provides for methods of preparing panels of solid-phase substrates that present native HLA antigens that are free from denatured antigens or panels of solid-phase substrates that present denatured HLA antigens that are free from native HLA antigens. The methods of preparing a panel of solid-phase substrates presenting native HLA antigens free from denatured HLA antigens, comprise the steps of: contacting a sample comprising HLA antigens with an antibody that is specific for denatured HLA antigens to form a complex comprising the denatured HLA antigen and the antibody, separating the complex from the sample, and isolating the native HLA antigens from the sample and presenting the native HLA antigens on a solid phase substrate. The term "free from denatured HLA antigens" refers to a solid-phase substrate that predominantly presents native HLA antigens and presents a negligible amount if any denatured HLA antigens.

The methods of preparing a panel of solid-phase substrates presenting denatured HLA antigens free from native HLA antigens, comprise the steps of: contacting a sample comprising HLA antigens with an antibody that is specific for native HLA antigens to form a complex comprising the native HLA antigens and the antibody, separating the complex from the sample, and isolating the denatured HLA antigens from the sample and presenting the denatured HLA antigens on a solid-phase substrate. The term "free from native HLA antigens" refers to a solid-phase substrate that predominantly presents denatured HLA antigens and presents a negligible amount if any native HLA antigens.

In one embodiment, the contacting step of these methods is carried out with an antibody that is bound to an affinity column. The denatured HLA antigens or native HLA antigens may be removed from any sample that comprises HLA antigens derived from such as a cell sample including mammalian, insect or bacteria cells.

BRIEF DESCRIPTION OF DRAWING

FIG. 1A-1B depict a comparison of positive control (PC) serum reaction pattern to control antigen beads (FIG. 1A) vs. denatured antigen beads (FIG. 1B). The Y-axis lists fluorescent intensities of each antigen beads that indicate the reactivity level. The bead ID and specificity of each antigen bead is listed along the X-axis. The reactions are sorted by the reactivity level from strong (left) to weak (right) along the X-axis. PC serum reacted strongly to B27, B7, B49, B67, B81, B42, B56, B57, B58, B53, 63, B8201, B73, and B50 on the control antigen beads; however, it only reacted relative strongly to Cw7 and Cw17 on the denatured antigen beads.

FIG. 6 depicts that absorption of antibodies that specifically bind to denatured HLA antigens did not affect serum reactivity to native HLA antigens.

DETAILED DESCRIPTION

Figure 1A:
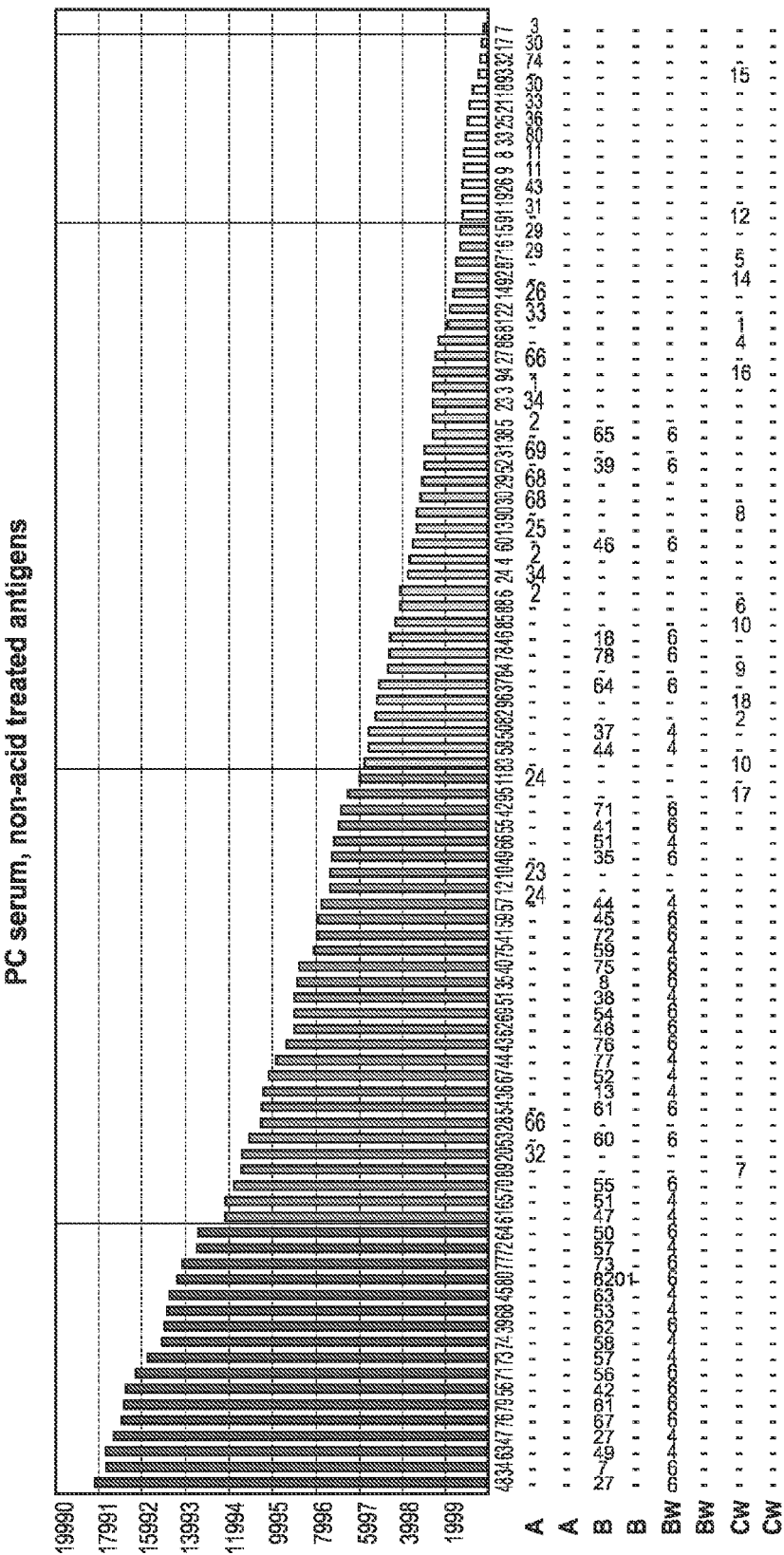

The experiments described herein suggest that antibodies to denatured HLA antigens are clinically significant especially for developing complete HLA antibody and HLA antigen profiles for virtual cross-matching blood and tissue donors and recipient pairs. Antibodies to denatured HLA antigens have been detected in untransfused male patients and in untransfused females who were not known to have been pregnant. These findings suggest that the cell-based assays may be missing clinically significant antibodies to denatured HLA antigens. Denatured antigens are not present on cells, so solid-phase assays are important for developing assays for denatured HLA antigens.

The experiments described in Example 2 demonstrate that denatured HLA antigens may be separated from native HLA antigens. A panel of β2m-free HLA heavy chain coated microparticles (denatured antigen beads) can be generated by treatment of the antigen presenting microparticles with low pH (as described in Example 1 and taught in Pei et al. (Visuals Clinical Histocompatability Workshop 2000, 9-10)). Using a denatured antigen presenting microparticle panel, it was determined for the first time that multiple polymorphic antibodies against denatured antigens existed in the sera, and the sera also contained antibodies against β2m-associated antigens. This multiplex assay allows one to distinguish antibodies against individual specificity of native vs. denatured antigens. With this tool, the antibodies to the denature antigens can be identified and their functions can be further studied.

In addition, the experiments described in Example 3 demonstrate that serum from some patients have a high reactivity to denatured HLA antigens, while these same patients do not have a high reactivity to the corresponding native HLA antigens. The experiments provide the HLA antigen profile for a positive control serum and two actual patients. The positive control serum has a low reactivity to the denatured HLA antigens (see FIG. 1). In patient sample #1, the serum was highly reactive to one HLA antigen (A30), the control beads comprise both denatured and native antigens so it is unknown whether this sample has reactivity to both denatured and native antigens (FIG. 2). Therefore, screening for reactivity to denatured antigens in this patient may not be imperative. However, patient sample #2 was highly reactive to 4 native HLA antigens and was highly reactive to 2 different denatured HLA antigens (FIG. 3). The B75 antigen was only be detected in the denatured antigen panel. Therefore, if patient #2 is not screened for reactivity to denatured antigens, it is likely that this patient will reject the transplanted organ. Therefore, this study suggests that it is imperative to screen for both native and denatured HLA antigens.

These experiments demonstrate that not all transplant recipients require screening for antibodies to denatured antigens, but some recipients in the general population, i.e. patient #2 described herein, are at a higher risk for rejection of a transplanted organ due to their reactivity to different native and denatured HLA antigens. Thus, there is a clinical significance to screening for antibodies that are highly reactive to native and denatured antigens.

Even though most reports relating to anti-HLA denatured antigens focus on the presence of reactivity to denatured class I antigens, the experiments presented in Example 3 demonstrate that the use of recombinantly expressed and purified individual α and β chain HLA class II antigens may be used to detect the presence of antibodies that specifically bind denatured HLA class II antigens. This assay allows for the detection of antibodies specific for denatured HLA class II antigens despite the lack of well-characterized monoclonal antibodies that allow for the verification of class II antigen denaturation.

The presence of antibodies that specifically bind to denatured HLA antigens may reduce the sensitivity of solid-phase antibody detection assays because a serum may have reactivity to denatured HLA antigens in a solid-phase assay but would not react to native HLA antigens in a cell-based assay. The reactivity to a denatured HLA antigen would be considered a false positive since the transplant recipient is unlikely to present denatured HLA antigens in vivo. The false positive results may negatively impact transplant tissue allocation because a prospective recipient may be turned away due to a false positive result. The experiments in Example 4 demonstrate that serum reactivity to denatured HLA antigens may be reduced or eliminated by absorption of the antibodies that specifically bind denatured HLA antigens using recombinantly expressed and purified single chain HLA antigens. Removal of serum reactivity to denatured HLA antigens allows for confirmation and enhanced detection of specific (transplant relevant) antibodies that bind to exposed epitopes on native HLA antigens (properly folded dimers). This assay should improve the concordance between solid-phase antibody tests using purified antigens and cell-based cross-match assays thereby reducing the number of false positive results. The invention is described in terms relating to detecting HLA specific antibodies and antigens using microbeads. However, the invention can be carried out using any type of solid-phase substrate known in the art and examples of such solid-phase substrates and assays are described herein.

HLA Antigens

The HLA locus is highly polymorphic in nature. As disclosed in the Nomenclature for Factors of the HLA System 2000 (Hum. Immunol.; 62(4):419-68, 2001) there are 124 HLA-A alleles, 258 HLA-B alleles, 74 HLA-C alleles, 221 HLA-DRB1 alleles, 19 DRB3 alleles, 89 DRB4 alleles, 14 DRB5 alleles, 19 DQA1 alleles and 39 DQB1 alleles, with new alleles being discovered continuously. As testament to this rapid progress, a April 2007 update by the WHO nomenclature Committee for Factors of the HLA System (www.anthonynolan.com/HIG/) showed there are 545 HLA-A alleles, 895 HLA-B alleles, 307 HLA-C alleles, 8 HLA-E alleles, 12 HLA-H alleles, 9 HLA-J alleles, 6 HLA-K alleles, 4 HLA-L alleles, 4 HLA-P alleles, 3 HLA-V alleles, 3 DRA alleles, 494 DRB1 alleles, 1 DRB2 alleles, 44 DRB3 alleles, 13 DRB4 alleles, 18 DRB5 alleles, 3 DRB6 alleles, 2 DRB7 alleles, 10 DRB8 alleles, 1 DRB9 alleles, 34 DQA1 alleles, 83 DQB1 alleles, 23 DPA1, 126 DPB1 alleles, 4 DMA alleles, 7 DMB alleles, 12 DOA alleles and 9 DOB alleles.

Methods of Detecting HLA Specific Antibodies

The invention provides for methods of detecting antibodies specific for denatured HLA antigen, antibodies specific for native HLA antigen and antibodies specific for HLA antigens in both the native and denatured conformation in a biological sample. The methods are carried out with solid-phase panels wherein the panel comprises substrates that present (or have immobilized) at least one or more selected native HLA antigens and substrates that present at least one or more selected denatured HLA antigens. Preferably, the HLA antigens are presented on microbeads and are denatured while attached to the microbead. For example, class I HLA antigens can be dissociated from βm2 while on the microbeads using low pH treatment such as the method provided in Pei et al. (Visuals Clinical Histocompatability Workshop 2000, 9-10). Class II HLA antigens coated on microbeads may be denatured by subjecting the microbeads to low PH conditions such as described in Tampé et al. (*Proc Natl Acad Sci USA.*, 88(23): 10667-10670, 1991). Binding of antibodies to the microbeads may be detected using methods such as FlowPRA (One Lambda) or Labscreen using Labscan flow cytometry.

The HLA antigens may be denatured while coated on a solid substrate using any method known to denatured proteins which will not damage the solid substrate. Exemplary treatments that will denature proteins include low or high pH, chaotropic agents, such as urea and guanidine hydrochloride at high concentrations such as 4 M to 8 M, detergents such as SDS and heat. For example, the antigen many be denatured in a buffer containing 0.3M Glycine-HCl pH2.7 with 1% BSA by mixing a 1:10 ratio of bead to denaturing buffer.

The invention also may be carried out with liquid-phase assays such as assays using column chromatography, affinity chromatography, thin layer chromatography, liquid-phase immunodiagnostic (LIPA) assays, liquid-phase chemiluminescent ELISA and liquid-phase immunoradiometric (IRMA) to name a few. The HLA antigens may be denatured while in the liquid phase or prior to being inserted into the liquid-phase assay.

Antigens of the invention may be a whole protein, a truncated protein, a fragment of a protein or a peptide. Antigens may be naturally occurring, genetically engineered variants of the protein, or may be codon optimized for expression in a particular mammalian subject or host. Generally, a B-cell epitope will include at least about 5 amino acids but can be as small as 3-4 amino acids. The antigens may be recombinantly expressed and purified from cells that either endogenously express the HLA antigens at a low level or do those that do not endogenously express the HLA antigens. Furthermore, the HLA antigens may be recombinantly expressed and presented on the cell surface, and the cells would be used in the methods of the invention.

Normally, an epitope will include between about 7 and 15 amino acids, such as, 9, 10, 12 or 15 amino acids. The term "antigen" denotes both subunit antigens, (i.e., antigens which are separate and discrete from a whole organism with which the antigen is associated in nature). Antibodies such as anti-idiotype antibodies, or fragments thereof, and synthetic peptide mimotopes, that is synthetic peptides which can mimic an antigen or antigenic determinant, are also captured under the definition of antigen as used herein.

Furthermore, for purposes of the present invention, an "antigen" refers to a protein, which includes modifications, such as deletions, additions and substitutions, generally conservative in nature, to the naturally occurring sequence, so long as the protein maintains the ability to elicit an immunological response, as defined herein. These modifications may be deliberate, as through site-directed mutagenesis, or may be accidental, such as through mutations of hosts which produce the antigens. Antigens of the present invention may also be codon optimized by methods known in the art to improve their expression or immunogenicity in the host.

Exemplary solid-phase assays such as assays of the invention may use solid substrates such as microparticles, magnetic particles such as ferromagnetic beads and paramagnetic beads, microtiter plates, membranes, filters, glass, metal, metal-alloy, anopol, polymers, nylon, plastic or microarrays such as protein chips. Microarrays may be of any material such as glass or silica. Binding on a microtiter plate may be detected using ELISA assays, RIA assays or other immunosorbent sandwich assays. Binding on a filter may be detected using immunoblotting techniques.

The solid-phase assays of the invention may be carried out with microparticles, microbeads, magnetic beads, beads or microspheres of any material, e.g. silica, gold, latex, polymers such as polystyrene, polysulfone and polyethyl, or hydrogel. Additional exemplary microparticles are encoded with the dyes and the antigens are immobilized to the encoded microparticles. The microparticles used in the methods of the invention are commercially available from sources such from Luminex Inc., Invitrogen (Carlsbad, Calif.), Polysciences Inc. (Warrington, Pa.) and Bangs Laboratories (Fishers, Ind.) to name a few.

The microparticles of the invention may comprise a detectable label or another identifying characteristic. The microparticles may comprise a single fluorescent dye or multiple fluorescent dyes. In one embodiment, the microparticles are internally labeled with fluorescent dyes and contain surface carboxyl groups for covalent attachment of biomolecules. In another embodiment, the microparticles are internally labeled with fluorescent dyes and contain a surface layer of Avidin for near covalent binding of biotin and biotinylated ligands. In another embodiment, the microparticles may comprise a combination of different dyes, such as a fluorescent and a non-fluorescent dye. For example, the microparticles may be labeled with E)-5-[2-(methoxycarbonyl)ethenyl]cytidine, which is a nonfluorescent molecule, that when subjected to ultraviolet (UV) irradiation yields a single product, 3-β-D-ribofuranosyl-2,7-dioxopyrido[2,3-d]pyrimidine, which displays a strong fluorescence signal. In another embodiment, the microparticles may comprise bar codes as an identifiable characteristic as described in U.S. Patent Publication No. US 20070037195.

In another embodiment, the microparticles may be nanocrystals or quantum dots. These nanocrystals are substances that absorb photons of light, then re-emit photons at a different wavelength (fluorophores). In addition, additional florescent labels, or secondary antibodies may be conjugated to the nanocrystals. These nanocrystals are commercially available form sources such as Invitrogen and Evident Technologies (Troy, N.Y.), The invention can be carried out with any system that detects the identifiable characteristic or label, such as FLOW cytometry. Detection of fluorescent labels may also be carried out using a microscope or camera that will read the image on the microparticles, such as the Bioarray BeadChip (Bioarray Solutions, Ltd., Warren, N.J.). The BeadChip format combines microparticle ("bead") chemistry with semiconductor wafer processing in which binding to the microparticle is recorded using an optical microscope and camera.

Biological samples includes whole blood, blood derivatives, red blood cell concentrates, plasma, serum, fresh frozen plasma, whole blood derived platelet concentrates, apheresis platelets, pooled platelets, intravenous gamma-globulin, cryoprecipitate, cerebrospinal fluid, tissues and cells such as epithelial cells, such as those collected from the buccal cavity, stem cells, leukocytes, neutrophils and granulocytes. The biological samples may be obtained from a human donor of tissue or cells intended for transplantation or a human donor of blood or blood derivatives intended for transfusion. The biological sample may be obtained from a healthy bone marrow donor or a subject of a paternity test. The biological sample may also be obtained from a human subject that is an intended recipient of a transplant or transfusion, or the human subject that is donating the tissue or organ intended for transplantation or transfusion. Alternatively, the biological sample may be obtained directly from tissues or cells that are intended for transplantation in a human recipient. In addition, the biological sample may be obtained from blood or blood derivatives that are intended for transfusion in a human recipient.

Methods of Detecting HLA Antigens

The invention provides for methods of detecting denatured HLA antigens in a biological sample. Antibodies specific for denatured HLA antigens are used to detect the presence of HLA antigens in a biological sample. Commercial antibodies that are specific for denatured HLA class I antigens include HB 10 (ATCC) and HB-296 (ATCC).

The antibodies of the invention may be polyclonal antibodies, monoclonal antibodies, antibody fragments which retain their ability to bind their unique epitope (e.g., Fv, Fab and F(ab)2 fragments), single chain antibodies and human or humanized antibodies. Antibodies may be generated by techniques standard in the art using an antigenic HLA epitope. See, e.g. Kohler et al., Nature, 256:495-497 (1975), Brodeur et al., Monoclonal Antibody Production Techniques and Applications, pp. 51-63 (Marcel Dekker, Inc., New York, 1987). Antibody molecules of the present invention include the classes of IgG (as well as subtypes IgG 1, IgG 2a, and IgG2b), IgM, IgA, IgD, and IgE.

The antibodies of the invention may be labeled for detection of binding within the biological sample. The antibodies may comprise a radioactive label such as $^{3}H$, $^{14}C$, $^{32}P$, $^{35}S$, or $^{125}I$. In addition, the labels may be a fluorescent or chemiluminescent compound, such as fluorescein isothiocyanate, phycoerythrin, rhodamine, or luciferin. The labels may be enzymes such as alkaline phosphatase, β-galactosidase, biotin and avidin or horseradish peroxidase (Bayer et al., Meth. Enz., 184:138-163 (1990)).

The antibodies specific for denatured HLA antigens may be attached to solid substrates such as membranes, beads, filters, glass, silicon, metal, metal-alloy, anopore, polymeric, nylon or plastic for detection of HNA-3 in a biological sample.

Specific binding of an antibody to a denatured HLA antigen within a biological sample may be carried out using Western blot analysis with immunoblotting, immunocytochemistry, immunohistochemistry, dot blot analysis, flow cytometry, ELISA assays or RIA assays. These techniques and other approaches are conventional in the art (See Sambrook et al., Molecular Cloning: A Laboratory Manual, cold Springs Harbor Laboratories (New York, 1989).

Kits

The invention also provides for kits to carryout the methods of the invention. In particular, the invention provides for kit for conducting a method of screening for antibodies specific for native and denatured HLA antigens. The antigens provided in the kit may be conjugated to solid substrates in the kit. Alternatively, the kit comprises solid substrates and antigens and the skilled artisan can conjugate the antigens to the solid substrates allowing for optimization of the antigens used in the assay. The kits may also comprise the reagents necessary to detect and measure antibodies, such as HLA antibodies for use as a positive control.

Kits according to the invention also may comprise components for detecting denatured HLA antigens and native HLA antigens in a biological sample. The kit can comprise an antibody that specifically binds to denatured HLA antigens. The antibodies provided in the kit may be conjugated to solid substrates in the kit. Alternatively, the kit comprises solid substrates and antibodies and the skilled artisan can conjugate the antibodies to the solid substrates allowing for optimization of the antibodies used in the assay. The kit may also comprise antigens to use as a positive control. The kits may also comprise the reagents necessary to detect and measure HLA antigens in a biological sample.

Kits useful for detecting denatured HLA antigens or antibodies specific for denatured HLA antigens may further comprise any components necessary to carry out the detection assays that are conventional in the art. For example, the kits may comprise buffers, loading dyes, gels such as polyacrylamide gels and molecular weight markers for preparing SDS-PAGE gels to carry out Western blots. The kits may also comprise filters, membranes blocking buffers, control buffers, isotype control antibodies, wash buffers or buffers and reagents for detection to carry out immunoblotting or dot blotting analysis such as labeled secondary antibodies. The kit may also comprise fixing reagents, blocking buffers, control buffers, wash buffers, staining dyes and detection reagents including anti-idio specific antibodies. Furthermore, the kits may comprise the necessary reagents and tools to carryout flow cytometry, ELISA assays, RIA assays or microtoxicity assays.

Other aspects and advantages of the present invention will be understood upon consideration of the following illustrative example.

EXAMPLES

Example 1

Method of Denaturing HLA Class I Antigens on Beads

To investigate the presence of antibodies specific for denatured HLA antigens, beads known to present native HLA antigens were subjected to denaturing conditions. FlowPRA Class I beads (FL1-30, FL1SP, One Lambda Inc.), Flow Single antigen beads (FL1HD, One Lambda Inc.), LABCreen class I PRA (LS1PRA, One Lambda Inc.) or LABCreen Single antigen beads (LS1A01, LS1A02, LS1A03, or LS1A04, One Lambda Inc.) were incubated with a pH 3 buffer containing 0.1 M sodium acetate for 30 minutes at room temperature. The beads were subsequently washed twice with PBS and resuspended in PBS.

Monoclonal antibodies BIH I (One Lambda, Inc.) and W6/32 (ATCC) are known to specifically bind to β2m-associated class I antigens and not denatured HLA antigens. Monoclonal antibodies HC10 (ATCC) or HB-296 (ATCC) are known to specifically bind β2m-free class I antigens (denatured HLA antigens) (Perosa et al., J. Immunol. 171: 1918-1926, 2003).

To confirm that low pH treated beads were denatured, a panel of treated beads were mixed with a panel of untreated (native) beads. These bead were incubated with the BIH I antibody or the W6/32 antibody. Biotinylated antibody (2 μg) in of PBS (95 μl) were incubated with the antigen presenting beads (5 μl) with or without acid treatment for 30 minutes at 20-25° C. with gentle rotation. The microbeads were washed 3 times with 1 ml wash buffer (One Lambda., Inc.) by centrifugation at 9000 g for 2 minutes and then incubated with 100 μl FITC or PE-conjugated Streptavidin (Jackson ImmunoResearch). The microbeads were then washed twice with 1 ml wash buffer, and then 0.5 ml fixing solution (PBS with 0.5% formaldehyde) was added to the beads. The beads were then analyzed by a flow cytometer or a Luminex machine.

The fluorescent intensity of the antibody binding to the bead indicates the reactivity level of the antibodies to either native or denatured antigens. This analysis demonstrated that the BIH I and the W6/32 antibodies did not significantly bind to the beads presenting the denatured HLA antigens. This experiment demonstrates that the low pH treatment denatured the HLA antigens presented on beads that are currently used for bead-based HLA screening.

Example 2

Separation of β2m-Free (Denatured) and β2m-Associated (Native) HLA Class I Antigens It was of interest to develop techniques for separating denatured and native HLA antigens. A panel of untreated HLA antigen-presenting beads was incubated with an antibody specific for native HLA antigens (W6/32) and an antibody specific for denatured HLA antigens (HB-296; ATCC). The antigens on the beads were purified from human cell lines, and the beads contain both β2m+ and β2m-free antigens because β2m may be disassociated from class I HLA antigens in vitro during antigen purification or other manipulation.

The denatured HLA antigens of the above-identified panel were separated from the native HLA antigens using HC10 affinity column absorption. HC10 is an antibody that is specific for denatured HLA antibodies. Mixture of native and denatured HLA class I antigens were diluted to about 10-50 μg/ml and run through an HC10 affinity column at a flow rate of 0.5 ml/min. The native antigen remained in the flow though and the denatured antigen bound to the HC10 affinity column. The denatured antigens were then further eluted from the HC10 affinity column with a high or low pH buffer (pH 11 or pH 3).

Using these techniques, β2m-associated and β2m-free antigens were separated. Separation of the denatured HLA antigens allows for selective screening of antibodies specific for denatured antigens. These techniques demonstrated that the mixture of β2m-associated and β2m-free antigens can be separated, which allows for the native and denatured antigens to be distinguished. In addition, this separation technique allows beads to present either denatured or native antigens.

Example 3

Screening HLA Antibodies with Antigen Beads

Sera samples from patients waiting for kidney transplant were screened for the presence of antibodies specific for denatured HLA antigens using panels of beads which present both native HLA antigens and denatured HLA antigens. Twenty microliters of serum were incubated with 5 μl of each of the antigen beads with or without acid treatment (as described in Example 1) for 30 minutes at 20-25° C. with gentle rotation. The microbeads were washed 3 times with 1 ml wash buffer (One Lambda., Inc.) by centrifugation at 9000 g for 2 minutes and then incubated with 100 μl FITC or PE-conjugated F(ab)2 fragment of goat anti-human IgG (Jackson ImmunoResearch). The microbeads were then washed twice with 1 ml wash buffer, and then 0.5 ml fixing solution (PBS with 0.5% formaldehyde) was added to the beads. The beads were then analyzed by a flow cytometer or a Luminex machine.

FIG. 1 depicts a comparison of positive control (PC) serum reaction pattern to control antigen beads (FIG. 1A) vs. denatured antigen beads (FIG. 1B). PC serum reacted strongly to HLA antigens B27, 7, 49, 67, 81, 42, 56, 57, 58, 53, 63, 8201, 73, and B50 on the control antigen beads, which were not treated with low pH and therefore present both native and denatured HLA antigens. However, the PC serum only reacted relative strongly to antigens Cw7 and Cw17 on the denatured antigen beads, which were treated with low pH.

Figure 2A:
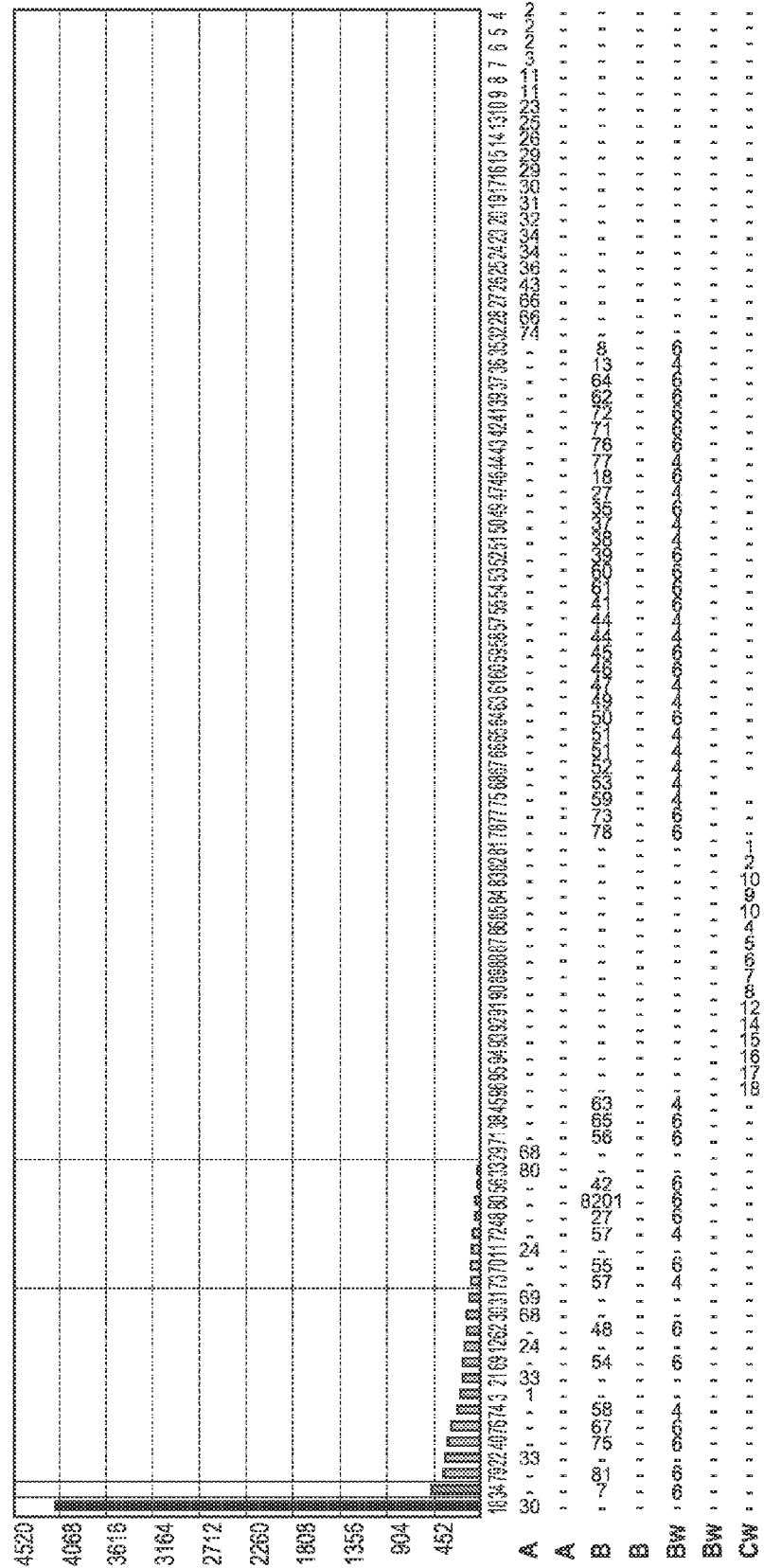
FIGS. 2A-2B depict a comparison of serum #1 reaction pattern to native (control) HLA antigen beads (FIG. 2A) vs. denatured HLA antigen beads (FIG. 2B). The Y-axis lists fluorescent intensities of each antigen bead that indicates the reactivity level of the serum to each antigen. The beads ID and specificity of each antigen beads is listed along the X-axis. Serum #1 reacted strongly to A30 on both control and denatured antigen beads.
Figure 2B:
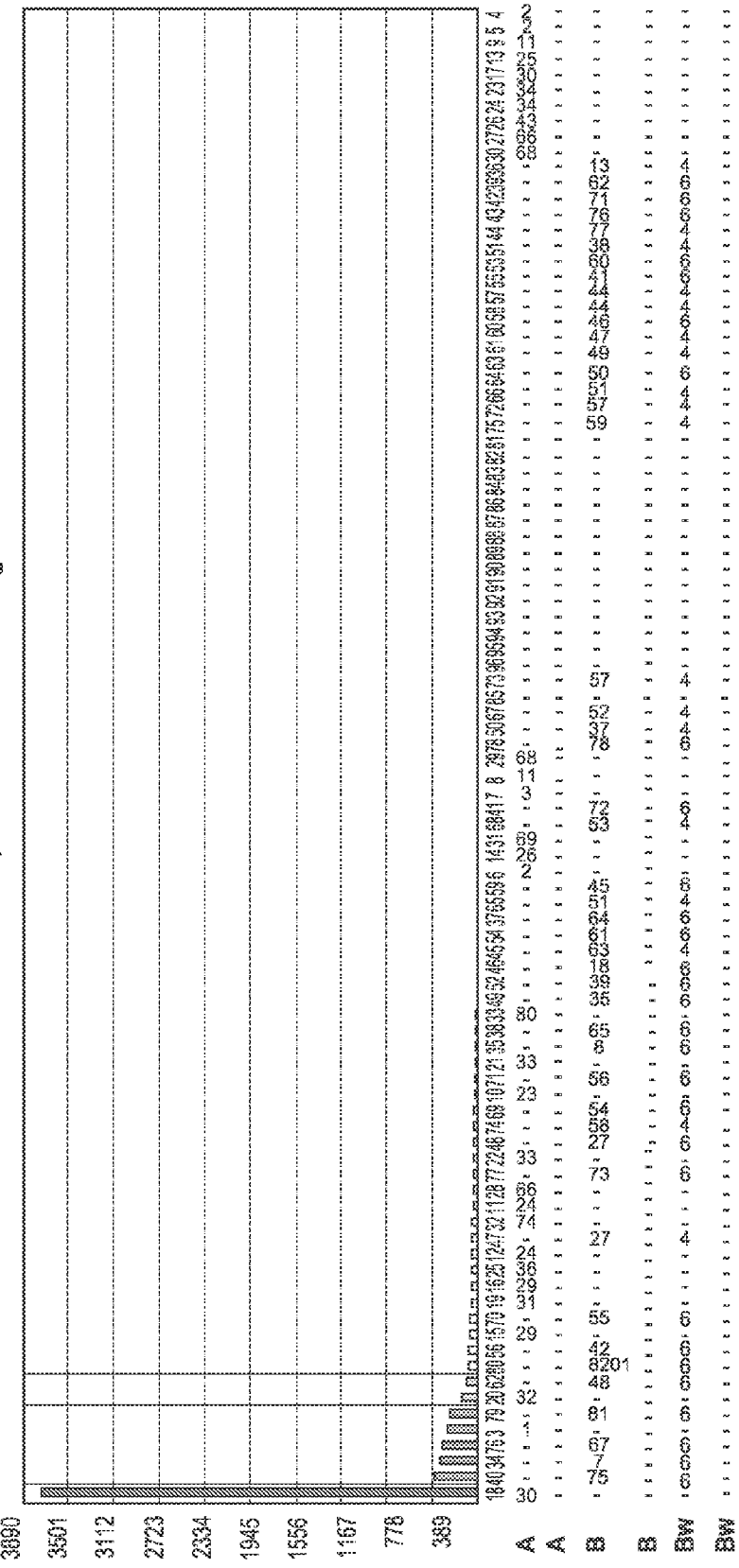

FIG. 2 depicts a comparison of serum #1 reaction pattern to control antigen beads (FIG. 2A) vs. denatured antigen beads (FIG. 2B) as described above. Serum #1 reacted strongly to HLA antigen A30 on both control (which contains both native and denatured antigens) and denatured antigen beads. The sample reacted strongly to the A30 antigen on the control beads that was a the mixture of HLA antigens in native and denatured conformation, and it reacted strongly with the beads that contained antigens in completely denatured conformation, indicating this patient contains antibodies to denatured A30 antigen.

Figure 3A:
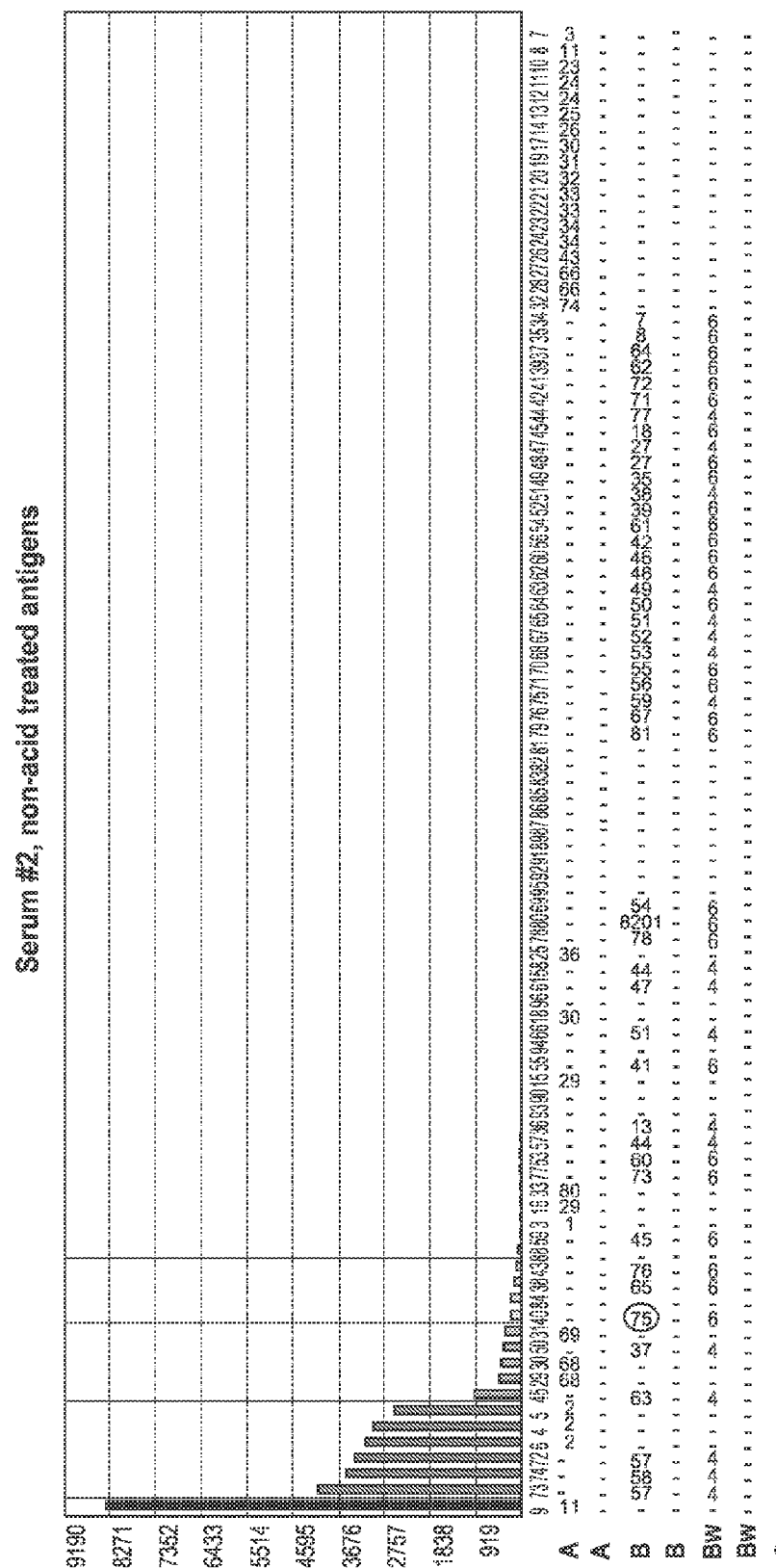
FIG. 3A-3B depicts a comparison of serum #2 reaction pattern to native (control) HLA antigen beads (FIG. 3A) vs. denatured HLA antigen beads (FIG. 3B). The Y-axis lists fluorescent intensities of each antigen bead that indicate the reactivity level. The beads ID and specificity of each antigen beads are listed along the X-axis. Serum #2 reacted to A2, A11, B57 and B58 on the control antigen beads; and it reacted to A2 and B75 on the denatured antigen beads.
Figure 3B:
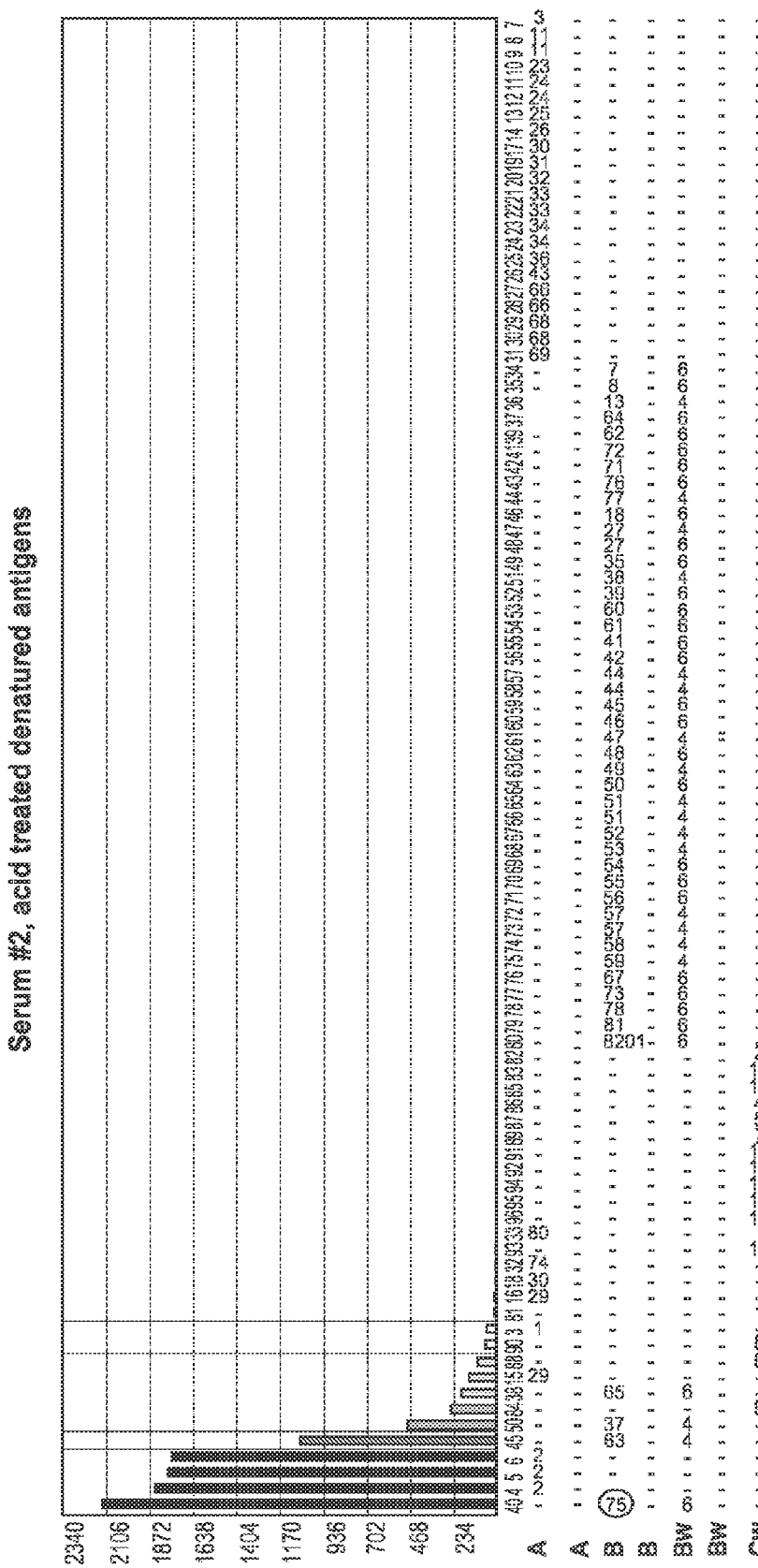

FIG. 3 depicts a comparison of serum #2 reaction pattern to control antigen beads (FIG. 3A) vs. denatured antigen beads (FIG. 3B) as described above. Serum #2 reacted to HLA antigens A2, A11, B57 and B58 on the control antigen beads; and it reacted to A2 and B75 on the denatured antigen beads. This sample has a strong reactivity to both native and denatured HLA antigens and these HLA antigens were different. Therefore, this assay suggests that failing to screen for reactivity to denatured antigens in addition to native antigens may result in rejection of the transplanted organ.

In addition, the data presented in FIGS. 2 and 3 demonstrate that the sera from actual patients contained antibodies specific for denatured antigens. Therefore, in view of current transplant rejection rates and the presence of antibodies specific for denatured HLA antibodies, it is likely that the denatured HLA antigens are clinically significant.

Example 4

Detection of Antibodies Reacting with denatured Class II HLA Antigens

Little is known about antibodies specific for denatured class II antigens, and there are no well characterized monoclonal antibodies that specifically bind to denatured class II HLA antigens and can verify the completion of Class II antigen denaturation. The present experiment describes an assay to identify antibodies that specifically bind to denatured class II HLA antigens in patient sera.

Individual α and β chain of HLA-DR class II antigens were expressed and purified from *Escherichia coli*. The purified single antigen chains were conjugated onto Luminex beads. Sera samples from patients were screened for the presence of antibodies specific for denatured class II HLA antigens using the LABScreen Single Antigen assay standard manufacturer's protocol (One Lambda, Inc.) and compared to the specialty beads and LSA01 Single Antigen beads. Table 1 shows the serum reactivity against denatured DRα chain (DRA*0101) and DRβ chain (DRB4*0101). The positive control was a known antibody that specifically binds to native HLA class II antigens. The negative control was a sample that did not contain any antibodies. The underlined mean fluorescence values (MFI) indicate positive binding by an antibody in the serum. Out of 8 pan-DR reacting serum, all had reactivity to DR β chain and 3 out of 8 sera also displayed reactivity to DRα chain.

TABLE 1

| | Allele | | | |
|---|---|---|---|---|
| | DRA*0101 | | DRB4*0101 | |
| | Concentration of sera | | | |
| | 1 µg | 2 µg | 1 µg | 2 µg |
| Positive control | 3489 | 3007 | 3202 | 3270 |
| Negative control | 1148 | 1041 | 2636 | 2934 |
| Serum 1 | 9417 | 9426 | 14239 | 14085 |
| Serum 2 | 20833 | 19307 | 24522 | 24078 |
| Serum 3 | 4681 | 4921 | 10282 | 10050 |
| Serum 4 | 15335 | 15038 | 20891 | 19527 |
| Serum 5 | 4231 | 4501 | 9739 | 9595 |
| Serum 6 | 4958 | 5450 | 20843 | 20690 |
| Serum 7 | 4466 | 5118 | 15633 | 16844 |
| Serum 8 | 6063 | 6242 | 22469 | 23439 |
| Serum 9 | 17169 | 18207 | 24182 | 23894 |
| Serum 10 | 4220 | 4057 | 11174 | 11308 |
| Serum 11 | 10090 | 9897 | 19662 | 19279 |

Table 2 shows the serum reactivity against denatured HLA-DR α chain (DRA*0101), HLA-DR β chain (DRB4*0101), HLA-DP α chain (DPA1*0103), HLA-DP β chain (DPB1*0101) and HLA-DQ β chain (DQB1*0201). The underlined Mean Fluorescent Values (MFI) indicates the positive reactions. The sera set out in Table 2 were known to be reactive to self alleles, and 2 of the 7 serum samples had reactivity to the HLA-DR β chain, HLA-DQ β chain and HLA-DP β chain.

TABLE 2

| Allele | DRA*0101 | | DRB4*0101 | | DPA1*0103 | | DPB1*0101 | | DQB1*0201 | |
|---|---|---|---|---|---|---|---|---|---|---|
| Conc. | 1 µg | 2 µg | 1 µg | 2 µg | 1 µg | 2 µg | 1 µg | 2 µg | 1 µg | 2 µg |
| Negative control | 526 | 376 | 1202 | 1472 | 665 | 701 | 1272 | 885 | 1867 | 1882 |
| Positive control | 3236 | 2306 | 4877 | 5701 | 1893 | 2249 | 3525 | 2814 | 3855 | 4160 |
| Serum 12 | 702 | 629 | 642 | 694 | 1534 | 1896 | 3107 | 2804 | 3385 | 3651 |
| Serum 13 | 2547 | 1981 | 3045 | 3516 | 2138 | 2257 | 3948 | 3144 | 5225 | 5516 |
| Serum 14 | 15890 | 11447 | 16350 | 16892 | 7845 | 7630 | 10982 | 7653 | 13390 | 13447 |
| Serum 15 | 3207 | 3156 | 3896 | 4581 | 4528 | 5000 | 6496 | 5639 | 6280 | 6971 |
| Serum 16 | 12149 | 8872 | 12966 | 13321 | 6824 | 6458 | 7638 | 5749 | 9222 | 9161 |
| Serum 17 | 6754 | 4479 | 10582 | 11733 | 5805 | 6944 | 9962 | 9478 | 11137 | 12212 |
| Serum 18 | 3397 | 2578 | 4301 | 4638 | 2564 | 2767 | 4722 | 3720 | 6731 | 6671 |
| Anti-HIgG | 15 | 15 | 15 | 14 | 12 | 14 | 11 | 10 | 10 | 23 |

Example 5

Absorption of Antibodies Against Denatured HLA Antigens

HLA Class I heavy chain and Class II α and β chain were expressed and purified from *E. coli*. The purified single chain antigens were conjugated onto paramagnetic particles (Spherotech, CM-025-10). The antigen coated beads were then incubated with test serum (known to react to denatured HLA antigens) for 30 minutes at room temperature. The bead particles were then separated from the serum using a magnetic field according to the manufacturer's instructions. The reactivity of the serum then was assayed using LABScreen Single Antigen beads (One Lambda Inc. LS1A04) using the standard manufacturer's protocol.

Serum sample 38 is known to contain antibodies which specifically bind to denatured HLA-A2 antigen. Serum 38 reactivity was tested for the following HLA Class I antigens for A2 (RA0101, RA 201, RA203, RA0206), A11 (RA 1101, RA1102), A23 (RA2301), A24 (RA2402, RA2403), A25 (RA 2501) A26 (RA2601), A29 (RA2901, RA2902), A30 (RA 3001, RA3002), A31 (RA3101), A32 (A3201), A33 (RA3301, RA3302), A34 (A3401, A3402), A36 (RA3601), A68 (RA6802), A80 (RA8001), B13/B4 (RB1302), B62/BW6 (RB1501), B71/B6 (RB1510), B27/BW6 (RB2708), B38/BW4 (RB380)1, B61/BW6 (RB4002), B46/BW6 (RB4601), B49/BW4 (RB4901), B51/BW4 (RB5102), B59/BW4 (RB5901), B78/B6 (RB7801), CW1 (RC0102), CW9 (RC0303), CW5 (RC0501), CW8 (RC0801), CW15 (RC1501), CW18 (RC1802), B61/BW6 (RB4006). Serum 38 was contacted with beads presenting purified HLA Class I heavy chain RA0101(A*0101), RA0201 (A*0201), RB0702 (B*0702) and denatured HLA-A2 antigen for absorption of antibodies specific for denatured HLA antigens. Only contacting with beads presenting A*0201 removed serum reactivity to Class I antigens: RA0201, RA0203, RA 0206, RA2301, RA2402 and RA3401 as shown in FIG. 4.

Serum sample 37 is known to contain antibodies which specifically bind to denatured HLA-A1,36. Serum 37 reactivity was tested for the HLA Class I antigens listed above. Serum 37 was contacted with beads presenting purified HLA Class I heavy chain RA0101(A*0101), RA0201 (A*0201), RB0702 (B*0702) and denatured HLA-A1,36 for absorption of antibodies specific for denatured HLA antigens. Only contacting with beads presenting A*0101 removed serum reactivity to Class I antigens: RA0101 and RA-3601 as shown in FIG. 5.

Figure 4:
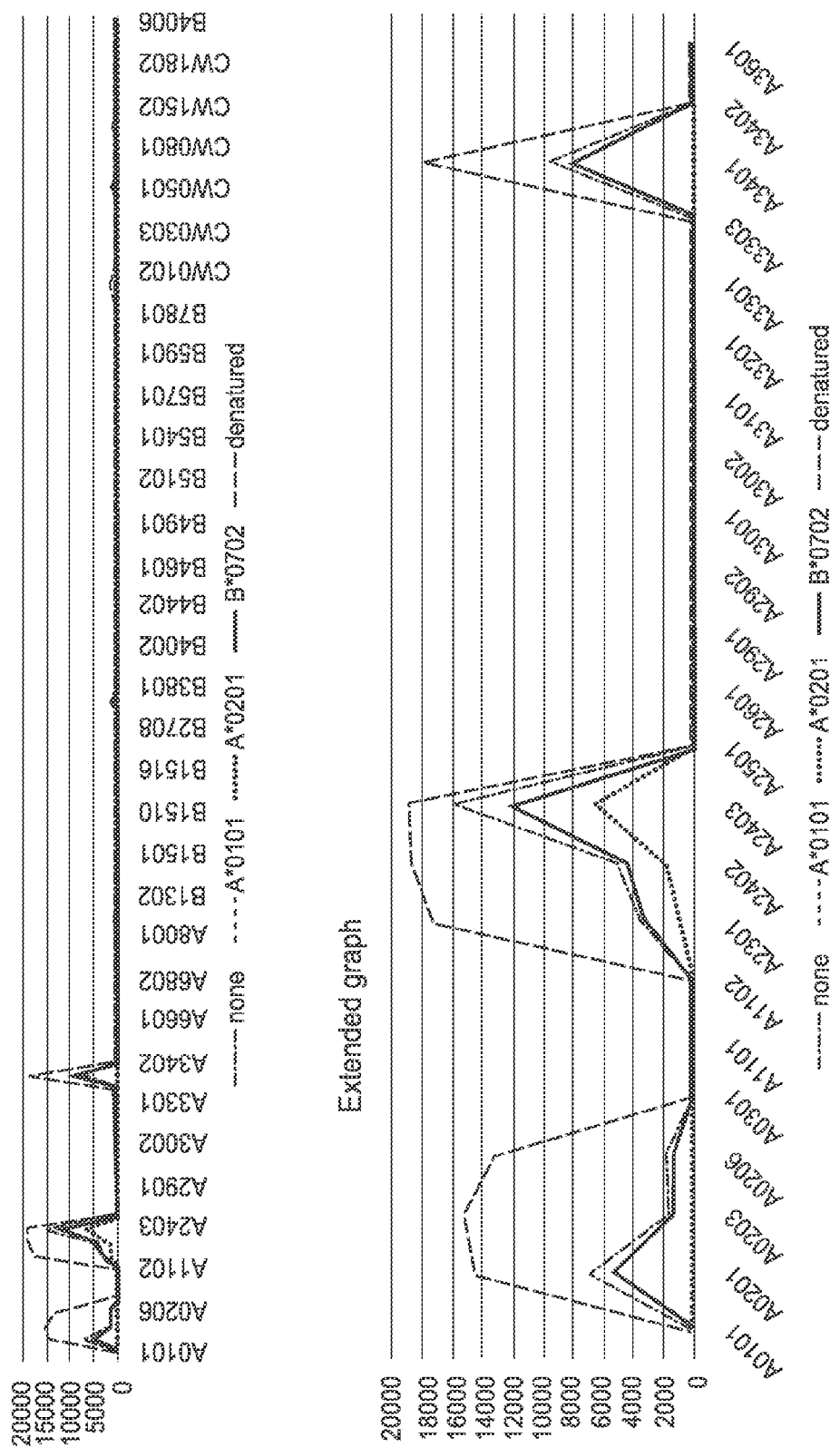
FIG. 4 depicts that contacting a serum sample with a bead presenting recombinant denatured HLA A2 antigen resulted in absorption of antibodies that specifically bind to denatured HLA A2 antigen.
Figure 5:
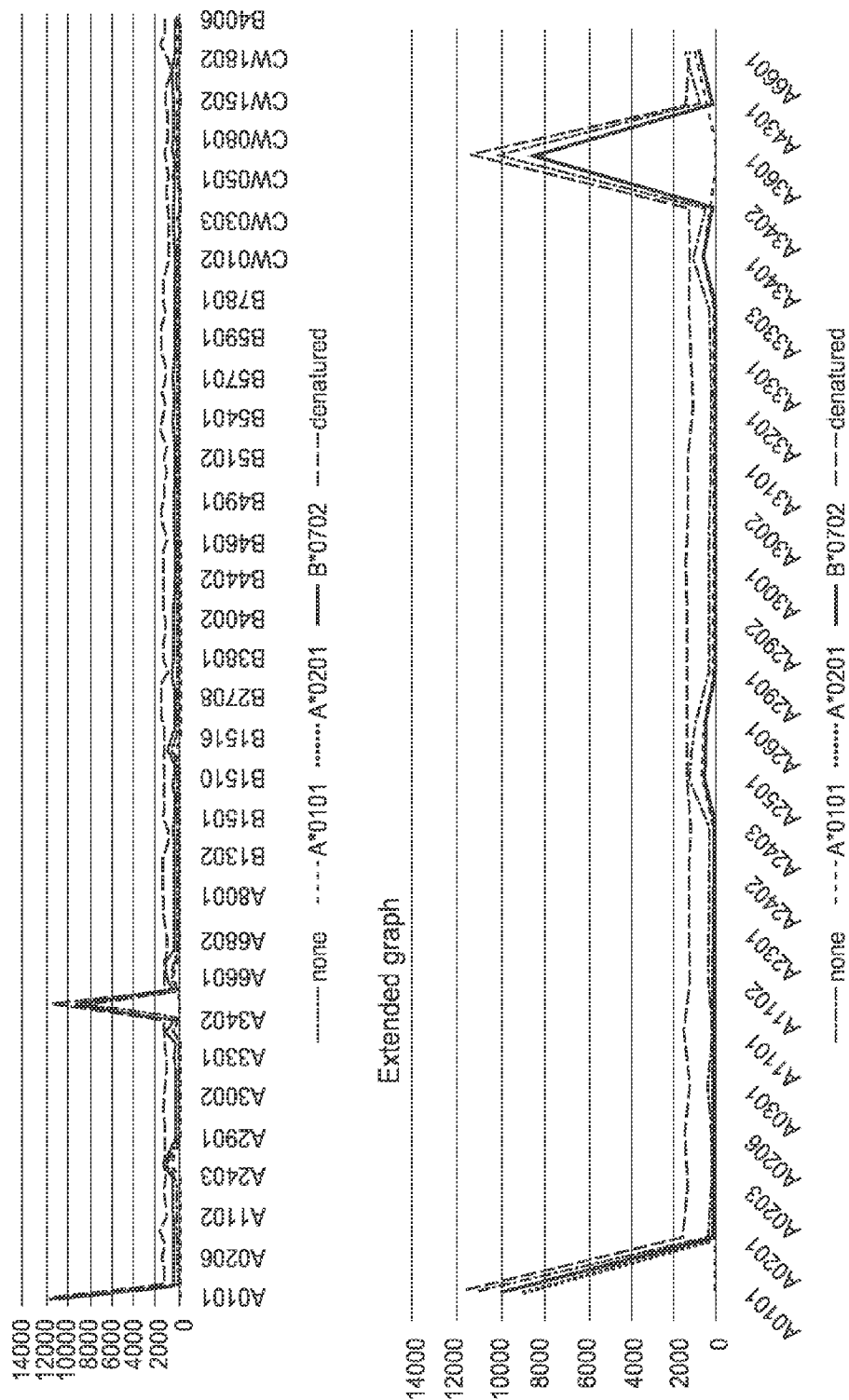
FIG. 5 depicts that contacting a serum sample with a bead presenting recombinant denatured HLA A1,36 antigen resulted in absorption of antibodies that specifically bind to denatured HLA A1 antigen.

FIGS. 4 and 5 are examples demonstrating that denatured HLA antigen coated magnetic beads remove all the antibody reactivity to the HLA antigens that share epitopes with the denatured HLA antigens used for absorption. This absorption process is antigen specific and did not remove antibody reactivity to native HLA antigens as shown in FIG. 6. specifically, serum 39 does not contain antibodies that specifically bind to denatured HLA antigens. Serum 39 reactivity was tested for the HLA Class I listed antigens listed above. Serum 39 was contacted with beads presenting purified HLA Class I heavy chain RA0101(A*0101), RA0201 (A*0201), RB0702 (B*0702) and denatured antigens for absorption of antibodies specific for denatured HLA antigens. The serum reactivity to native antigens was not affected when the serum was absorbed with denatured A1, A2 or B7 coated beads.

This analysis demonstrates that serum reactivity to denatured HLA antigens can be significantly reduced, if not eliminated, by absorption with recombinant single chain HLA antigens, which permits confirmation and enhanced detection of specific (transplant relevant) antibodies that target exposed epitopes on native HLA antigens (properly folded dimmers). This approach should improve the concordance between solid-phase antibody detection assays using purified HLA antigens and cell-based cross-matched assays, and thereby reduce false positive results determined by the solid-phase assays.

Numerous modifications and variations in the practice of the invention are expected to occur to those skilled in the art upon consideration of the presently preferred embodiments thereof. Consequently, the only limitations which should be placed upon the scope of the invention are those which appear in the appended claims.

What is claimed:

1. A method of screening comprising the steps of:
   contacting a first solid phase substrate having immobilized thereon said denatured human leukocyte antigen (HLA) with a serum sample comprising antibodies that specifically bind said denatured HLA antigen to form an antibody/antigen complex,
   separating the antibody/antigen complex from the serum sample to generate a serum sample essentially free of antibodies that specifically bind said denatured HLA antigen,
   contacting the serum sample that is essentially free of antibodies that specifically bind said denatured HLA antigen with a second solid-phase substrate having native HLA antigen immobilized or attached thereto, and
   detecting binding of an antibody in said serum sample that is essentially free of antibodies that specifically bind to denatured HLA antigen to the HLA antigen immobilized or attached to the second solid-phase substrate in order to identify the presence of antibodies specific for the native HLA antigen.

2. A method of screening, comprising the steps of:
   contacting a cell that presents denatured human leukocyte antigen (HLA) with a serum sample comprising antibodies that specifically bind said denatured HLA antigen to form an antibody/antigen complex,
   separating the antibody/antigen complex from the serum sample to generate a serum sample essentially free of antibodies that specifically bind said denatured HLA antigen,
   contacting the serum sample that is essentially free of antibodies that specifically bind said denatured HLA antigen with a solid-phase substrate having native HLA antigen immobilized or attached thereto, and
   detecting binding of an antibody in said serum sample that is essentially free of antibodies that specifically bind denatured HLA antigen to the HLA antigen immobilized or attached to the solid-phase substrate in order to identify the potential presence of antibodies which are specific for native HLA antigen.

3. The method of claim 1 or 2, wherein the HLA antigen is a HLA class I antigen.

4. The method claim 1 or 2, wherein the HLA antigen is a HLA class II antigen.

5. The method of claim 1 or 2, wherein the solid-phase substrate is selected from the group consisting of microparticles, microbeads, magnetic beads and an affinity purification column.

6. The method of claim 1 or 2, wherein the serum sample is obtained from a human subject that is a transplant or transfusion recipient.

7. The method of claim 1 or 2, wherein the serum sample is obtained from a human subject that is a transplant or transfusion donor.

* * * * *